United States Patent
Connolly et al.

(10) Patent No.: US 10,342,865 B2
(45) Date of Patent: Jul. 9, 2019

(54) METHOD FOR TREATING EPSTEIN-BARR VIRUS—POSITIVE CANCER WITH IMMUNOTHERAPY

(71) Applicants: AGENCY FOR SCIENCE, TECHNOLOGY AND RESEARCH, Singapore (SG); TESSA THERAPEUTICS PTE. LTD., Singapore (SG); SINGAPORE HEALTH SERVICES PTE. LTD., Singapore (SG)

(72) Inventors: John Connolly, Singapore (SG); Richard Hopkins, Singapore (SG); Han Chong Toh, Singapore (SG)

(73) Assignees: TESSA THERAPEUTICS PTE. LTD, Singapore (SG); SINGAPORE HEALTH SERVICES PTE. LTD., Singapore (SG); AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 0 days.

(21) Appl. No.: 15/594,167

(22) Filed: May 12, 2017

(65) Prior Publication Data

US 2017/0312355 A1 Nov. 2, 2017

Related U.S. Application Data

(63) Continuation of application No. PCT/SG2016/050441, filed on Sep. 9, 2016.

(30) Foreign Application Priority Data

Dec. 4, 2015 (SG) .............................. 10201509979S

(51) Int. Cl.
| | | |
|---|---|---|
| *A61K 35/17* | (2015.01) | |
| *C12Q 1/68* | (2018.01) | |
| *C12Q 1/6886* | (2018.01) | |
| *G01N 33/574* | (2006.01) | |
| *A61K 39/245* | (2006.01) | |
| *C12N 7/00* | (2006.01) | |
| *C12Q 1/70* | (2006.01) | |
| *A61K 39/00* | (2006.01) | |

(52) U.S. Cl.
CPC ............ *A61K 39/245* (2013.01); *A61K 35/17* (2013.01); *C12N 7/00* (2013.01); *C12Q 1/68* (2013.01); *C12Q 1/6886* (2013.01); *C12Q 1/701* (2013.01); *C12Q 1/705* (2013.01); *G01N 33/574* (2013.01); *G01N 33/57407* (2013.01); *G01N 33/57423* (2013.01); *G01N 33/57438* (2013.01); *G01N 33/57446* (2013.01); *A61K 2039/5158* (2013.01); *A61K 2039/545* (2013.01); *A61K 2039/57* (2013.01); *A61K 2039/572* (2013.01); *A61K 2039/585* (2013.01); *C12N 2710/16234* (2013.01); *C12N 2710/16271* (2013.01); *C12Q 2600/106* (2013.01); *C12Q 2600/118* (2013.01); *C12Q 2600/158* (2013.01); *G01N 2333/05* (2013.01); *G01N 2333/521* (2013.01); *G01N 2333/57* (2013.01); *G01N 2800/52* (2013.01)

(58) Field of Classification Search
None
See application file for complete search history.

(56) References Cited

U.S. PATENT DOCUMENTS 8,541,185 B2    9/2013   Oved et al.

FOREIGN PATENT DOCUMENTS

| WO | WO 2007/045996 A1 | 4/2007 |
| WO | WO 2012/149416 A2 | 11/2012 |
| WO | WO 2015/043614 A1 | 4/2015 |

OTHER PUBLICATIONS

Marrao et al., BMC Cancer, 2014, 14:665. (Year: 2014).*
Baumforth et al. (2008) The American Journal of Pathology 173(1):195-204 "Expression of the Epstein-Barr Virus-Encoded Epstein-Barr Virus Nuclear Antigen 1 in Hodgkin's Lymphoma Cells Mediates Up-Regulation of CCL20 and the Migration of Regulatory T Cells".
Cai et al. (2014) Medicine 93(22):1-7 "Increased Serum Levels of Macrophage Inflammatory Protein-3α and Cystatin A Predict a Poor Prognosis of Nasopharyngeal Carcinoma".
Chang et al. (2010) Head and Neck DOI:1001/hed.21557 "Multiplexed Immunobead-based Profiling of Cytokine Markers for Detection of Nasopharyngeal Carcinoma and Prognosis of Patent Survival".
Chang et al. (2014) World J Gastroenteriol 20(16):4586-4596 "Inflammation-related factors predicting prognosis of gastric cancer".
Chia et al. (2014) Molecular Therapy 22(1): 132-139 "Adoptive T-cell Transfer and Chemotherapy in the First-line Treatment of Metastatic and/or Locally Recurrent Nasopharyngeal Carcinoma".
Comoli et al. (2005) 23(35):8942-8949 "Cell Therapy of Stage IV Nasopharyngeal Carcinoma With Autologous Epstein-Barr Virus-Targeted Cytotoxic T Lumphocytes".
International Search Report and Written Opinion for PCT/SG2016/050441 dated Nov. 14, 2016.
Lau et al. (2007) British Journal of Cancer 96:617-622 "Increase in circulating Foxp3 + CD4 + CD25$^{high}$ regulatory T cells in nasopharyngeal carcinoma patients".

(Continued)

*Primary Examiner* — Nicole Kinsey White
(74) *Attorney, Agent, or Firm* — Adsero IP

(57) ABSTRACT

A method for predicting whether a patient will be a long-term survivor on treatment of a disease by adoptive cell transfer (ACT), is disclosed comprising: (i) analyzing a blood-derived sample obtained from the patient for one or more prognostic markers of long-term survival on treatment of a disease by ACT, and; (ii) based on the analysis of step (i), predicting whether the patient will be a long-term survivor on treatment of the disease by ACT. Also disclosed are methods for treating a patient by ACT, methods for selecting a patient for treatment by ACT, and methods for selecting a patient for treatment of a disease by ACT.

14 Claims, 27 Drawing Sheets

(56) References Cited

OTHER PUBLICATIONS

Li et al. (2011) Int. J. Biol. Sci. 7(5):607-617 "Immunophenotyping at the Time of Diagnosis Distinguishes Two Groups of Nasopharyngeal Carcinoma Patients: Implications for Adoptive Immuno-therapy".
Louis et al. (2009) Blood 113(11):2442-2450 "Enhancing the in vivo expansion of adoptively transferred EBV-specific CTL with lymphodepleting CD45 monoclonal antibodies in NPC patients".
Toh et al. (2012) The Lancet.com/Oncology 13:568-569 "Personalised medicine in nasopharyngeal cancer".
Wang et al. (2014) Immunotherapy 6(12):1265-1278 "Current advances in T-cell-based cancer immunotherapy".

\* cited by examiner

Table 1

|  |  | T-1 | T0 | T1 |
|---|---|---|---|---|
| WBC | Spearman r | -0.2263 | -0.3247 | -0.4367 |
|  | p-value | 0.1981 | 0.061 | *0.0111* |
| Neutrophils | Spearman r | -0.167 | -0.1051 | -0.3188 |
|  | p-value | 0.3451 | 0.554 | *0.0706* |
| Lymphocytes | Spearman r | 0.2251 | 0.3299 | 0.456 |
|  | p-value | 0.2006 | 0.0567 | *0.0076* |
| Monocytes | Spearman r | 0.02828 | -0.1329 | -0.105 |
|  | p-value | 0.8739 | 0.4536 | 0.561 |

Table 2

|  |  | T0 | T1 |
|---|---|---|---|
| IFNg | Spearman r | -0.04045 | 0.4637 |
|  | p-value | 0.8511 | *0.0395* |
| EBV DNA | Spearman r | -0.8818 | -0.8725 |
|  | p-value | *0.0007* | *0.0001* |
| CCL20 | Spearman r | -0.3951 | -0.5472 |
|  | p-value | *0.0339* | *0.0014* |
| CXCL10 | Spearman r | -0.2425 | -0.3155 |
|  | p-value | 0.1671 | 0.0737 |

Table 3

| Node | Comment | G-test | p-value | Node | Comment | G-test | p-value |
|---|---|---|---|---|---|---|---|
| CD68 | | 25.6321 | 0.00% | RIPK2 | | 14.9087 | 0.49% |
| LYN | | 18.9824 | 0.08% | CFD | | 6.8513 | 3.25% |
| S100A12 | | 16.0967 | 0.03% | CCL3 | | 9.4611 | 0.88% |
| S100A8 | | 16.0967 | 0.03% | IRAK1 | | 12.6548 | 0.18% |
| LILRA5 | | 19.5592 | 0.06% | CD8B | | 12.6548 | 0.18% |
| LILRA2 | | 12.6548 | 0.18% | CD8A | | 8.9097 | 1.16% |
| CCL3L1 | | 13.1642 | 1.05% | CR1 | | 17.7032 | 0.14% |
| S100A9 | | 12.4488 | 0.20% | CD96 | | 9.6182 | 0.82% |
| ICAM1 | | 13.4633 | 0.92% | CYBP2 | | 9.6182 | 0.82% |
| IGF1R | | 9.6182 | 0.82% | MAF | | 9.6182 | 0.82% |
| CD7 | | 11.1156 | 0.39% | IFI27 | | 12.6548 | 0.18% |
| LILRB4 | | 21.4721 | 0.03% | CSF3R | | 4.2733 | 11.81% |
| CD36 | | 16.1435 | 0.28% | THBS1 | | 11.6529 | 0.29% |
| BST1 | | 13.3248 | 0.98% | ETS1 | | 4.2473 | 11.96% |
| IFNGR1 | | 7.8656 | 1.96% | CLEC7A | | 15.0967 | 0.03% |
| TLR4 | | 8.6354 | 7.09% | CXCL2 | | 11.7112 | 1.96% |
| LRP1 | | 12.4488 | 0.20% | IL8 | | 16.8312 | 0.21% |
| MSR1 | | 15.5298 | 0.04% | PLAUR | | 9.6182 | 0.82% |
| CCR1 | | 15.4178 | 0.39% | NLRP3 | | 9.6182 | 0.82% |
| CSF2RB | | 12.3965 | 0.20% | TREM1 | | 20.2311 | 0.05% |
| CXCL16 | | 15.5298 | 0.04% | BCL6 | | 8.9097 | 1.16% |

Figure 9

Table 4

| Node | Comment | G-test (Data) | Degrees of Freedom (Data) | p-value (Data) | Node | Comment | G-test (Data) | Degrees of Freedom (Data) | p-value (Data) |
|---|---|---|---|---|---|---|---|---|---|
| [Factor_0] | MIF_(5) | 20.113 | 2 | 1.00E-06 | [Factor_10] | S100A8_(4) | 7.7176 | 1 | 5.50E-03 |
| MIF | | 20.113 | 2 | 1.00E-06 | S100A8 | | 7.7176 | 1 | 5.50E-03 |
| [Factor_4] | CD68_(5) | 16.3703 | 2 | 3.00E-04 | IFI27 | | 12.6548 | 1 | 4.00E-04 |
| [Factor_5] | EBV_DNA_L_(4) | 16.0967 | 1 | 1.00E-04 | KLRB1 | | 9.0687 | 2 | 1.07E-02 |
| EBV_DNA_L | | 16.0967 | 1 | 1.00E-04 | ETS1 | | 6.889 | 1 | 8.70E-03 |
| CXCL16 | | 14.3274 | 1 | 2.00E-04 | LILRA5 | | 12.5729 | 2 | 1.90E-03 |
| [Factor_16] | CXCL16_(3) | 14.3274 | 1 | 2.00E-04 | BST1 | | 5.7712 | 2 | 5.58E-02 |
| CD68 | | 18.2503 | 2 | 1.00E-04 | [Factor_21] | IFNGR1_(3) | 11.0796 | 1 | 9.00E-04 |
| RIPK2 | | 12.1 | 2 | 2.40E-03 | CD8B | | 20.8909 | 2 | 0.00E+00 |
| CD3G | | 12.6548 | 2 | 1.80E-03 | IFNGR1 | | 7.8296 | 1 | 5.10E-03 |
| MIP3a_L | | 12.6548 | 1 | 4.00E-04 | LYN | | 9.0508 | 2 | 1.08E-02 |
| S100A9 | | 10.3436 | 2 | 5.70E-03 | TLR2 | | 7.7292 | 2 | 2.10E-02 |
| IP-10_L | | 12.5729 | 2 | 1.90E-03 | S100A12 | | 4.2112 | 1 | 4.02E-02 |
| [Factor_1] | LILRA5_(5) | 15.8571 | 2 | 4.00E-04 | CD7 | | 5.2935 | 2 | 7.09E-02 |
| FCGR2A | | 6.9438 | 2 | 3.11E-02 | IRAK1 | | 12.6548 | 1 | 4.00E-04 |
| MSR1 | | 14.3274 | 1 | 2.00E-04 | [Factor_26] | THBS1_(2) | 12.4806 | 1 | 4.00E-04 |
| LGALS3 | | 9.1628 | 1 | 2.50E-03 | THBS1 | | 18.2503 | 2 | 1.00E-04 |
| PNMA1 | | 8.0583 | 2 | 1.78E-02 | TLR4 | | 6.8957 | 2 | 3.18E-02 |
| IL-6_L | | 7.7074 | 1 | 5.50E-03 | LRP1 | | 10.6121 | 2 | 5.00E-03 |
| | | | | | CR1 | | 9.6182 | 1 | 1.90E-03 |

Figure 21

Table 5

| Node | Comment | G-test (Data) | Degrees of Freedom (Data) | p-value (Data) | Node | Comment | G-test (Data) | Degrees of Freedom (Data) | p-value (Data) |
|---|---|---|---|---|---|---|---|---|---|
| [Factor_21] | CEACAM8_(3) | 17.0702 | 1 | 1.00E-06 | FEZ1 | | 8.7242 | 2 | 1.28E-02 |
| [Factor_32] | CD8B_(3) | 15.3658 | 2 | 5.00E-04 | LTB | | 10.1333 | 2 | 6.30E-03 |
| [Factor_30] | TCF7_(3) | 13.9363 | 1 | 2.00E-04 | IFITM1 | | 4.1626 | 2 | 1.25E-01 |
| CEACAM8 | | 11.4761 | 1 | 7.00E-04 | NFATC3 | | 8.429 | 1 | 3.70E-03 |
| CD8B | | 11.9131 | 2 | 2.80E-03 | CD96 | | 9.4495 | 2 | 8.90E-03 |
| CD8A | | 12.5173 | 2 | 1.90E-03 | [Factor_15] | ITK_(4) | 9.692 | 1 | 1.90E-03 |
| CD28 | | 11.1181 | 1 | 9.00E-04 | ITK | | 9.692 | 1 | 1.90E-03 |
| CD68 | | 11.1181 | 1 | 9.00E-04 | LCK | | 6.8478 | 2 | 3.26E-02 |
| [Factor_43] | CD68_(2) | 11.1181 | 1 | 9.00E-04 | IL7R | | 14.7743 | 1 | 1.00E-04 |
| TCF7 | | 8.7262 | 1 | 3.10E-03 | LRRN3 | | 12.8737 | 2 | 1.60E-03 |
| G-CSF_L | | 8.7262 | 1 | 3.10E-03 | [Factor_1] | CD5_(5) | 10.0575 | 3 | 1.81E-02 |
| CXCR3 | | 6.781 | 2 | 3.37E-02 | [Factor_33] | IL2RG_(3) | 9.6147 | 2 | 8.20E-03 |
| TNFSF15 | | 6.3319 | 1 | 1.19E-02 | KLRB1 | | 6.2338 | 1 | 1.25E-02 |
| [Factor_3] | ETS1_(5) | 11.7656 | 2 | 2.80E-03 | [Factor_20] | IL16_(4) | 6.2359 | 2 | 4.42E-02 |
| ITGB2 | | 4.4714 | 2 | 1.07E-01 | ITGA6 | | 2.8375 | 2 | 2.42E-01 |
| ETS1 | | 11.2922 | 1 | 8.00E-04 | CD3E | | 6.5831 | 2 | 3.72E-02 |
| [Factor_57] | JAK3_(2) | 4.2493 | 1 | 3.93E-02 | CD5 | | 8.2623 | 2 | 4.37E-02 |
| JAK3 | | 7.1161 | 2 | 2.85E-02 | IL21R | | 8.4683 | 2 | 3.94E-02 |
| CCR7 | | 4.7404 | 2 | 9.35E-02 | FLT3LG | | 6.6811 | 2 | 3.54E-02 |
| [Factor_50] | CCR7_(2) | 4.5497 | 1 | 3.29E-02 | [Factor_36] | FLT3LG_(3) | 6.0297 | 1 | 1.41E-02 |

Figure 23

METHOD FOR TREATING EPSTEIN-BARR VIRUS—POSITIVE CANCER WITH IMMUNOTHERAPY

RELATED APPLICATIONS

This application is a continuation application of PCT/SG2016/050441, filed Sep. 9, 2016, which claim priority to Singapore Application No. 10201509979S, filed Dec. 4, 2015, all of which are incorporated herein by reference in their entirety.

FIELD OF THE INVENTION

The present invention relates to treatment of disease by adoptive cell transfer (ACT), and in particular to the prediction of long-term survival on treatment of a disease by ACT based on analysis of correlates of long-term survival in blood or blood-derived samples obtained from patients.

BACKGROUND OF THE INVENTION

The following description provides a summary of information relevant to the present disclosure and is not an admission that any of the information provided or publications referenced herein is prior art to the present disclosure.

Epstein-Barr virus (EBV)-positive nasopharyngeal carcinoma (NPC) represents a significant health-care problem for South-East Asia. The incidence rate of NPC in South-East Asian males is 10 to 21.4 per 100 000 (Chang et al., Virus Res (2009) 143: 209-221). Current therapies are effective in controlling and curing non-metastasized NPC, however treatments for metastatic disease are limited. The median survival time for patients with the disseminated form of disease ranges from 11 to 22 months (Wee et al., J Clin Oncol (2005) 23: 6730-6738). An emerging alternative to chemotherapy is the use of immune-therapy strategies, which have focused on increasing the immune response to viral antigens.

Experimental immunotherapies have included dendritic cell (DC) vaccination (Gerdemann et al., Mol Ther (2009) 17: 1616-1625; Chia et al., Ann Oncol (2012) 23: 997-1005; Moosmann et al., Blood (2010) 115: 2960-2970), checkpoint inhibitor blockade (NCCT02460224; NCT02339558; Hamid O, Robert C, Daud A, et al. Safety and tumor responses with lambrolizumab (anti-PD-1) in melanoma. N Engl J Med 2013; 369:134-44), cytotoxic-T-lymphocyte (CTL) infusion (Louis et al., Blood (2009) 113: 2442-2450; Straathof et al., Blood (2005) 105: 1898-1904; Louis et al., J Immunother (2010) 33: 983-990) or expansion (Smith et al., Cancer Res. (2012) 72: 1116-1125), and CAR-T therapy. The cellular strategies have the end objective of inducing a cytotoxic T-cell response that is capable of directly killing virally infected tumors. Whilst there has been great progress in the application of checkpoint inhibitor blockade against tumors, their use against NPC has been limited. Efficacy of the therapeutic PD-1 antibody, Pembrolizumab, against NPC resulted in a median progression free survival rate of 5.6 months (Hamid O, Robert C, Daud A, et al. Safety and tumor responses with lambrolizumab (anti-PD-1) in melanoma. N Engl J Med 2013; 369:134-44). Furthermore, to date there has been no identification of a reliable biomarker to predict checkpoint inhibitor efficacy. CAR-T therapy has shown much promise against melanomas and lymphomas but has shown limited efficacy in clearing solid tumors. Similar to checkpoint inhibitor blockade, there has been no clear identification of factors that contribute to this failure. Identification of a series of biomarkers that could identify both how well patients will respond to therapy and when they will fail to respond would be invaluable for the health-care community.

This lack of efficacy of CAR-T therapies against solid tumors has been hypothesized to be partially attributable to an immunosuppressive state within the tumor microenvironment. During the establishment of the tumor an immunosuppressive environment is induced, in which regulatory T cells (Treg) contribute and play a role in the maintenance of this phenotype. Treatment with the chemotherapeutic gemcitabine in a variety of murine cancer models have shown to selectively deplete the Treg population without effecting the CTL population (Suzuki et al., Clin Cancer Res (2005) 11: 6713-6721; Nowak et al., Cancer Res (2002) 62: 2353-2358; Shevchenko et al., Int J Cancer (2013) 133: 98-107). Studies of the effects of gemcitabine on the Treg compartment in humans have so far been limited but early reports are showing that treatment results in a similar contraction of the regulatory subset both in vitro (Kan et al., Anticancer Res (2012) 32: 5363-5369) and in vivo (Rettig et al., Int J Cancer (2011) 129: 832-838).

Another regulatory cell type that is of increasing interest are the myeloid-derived suppressor cells (MDSCs). MDSCs are a population of myeloid cells that are expanded in the presence of various cancers. In humans MDSCs are a heterogeneous population but can be broadly defined as HLA-DR−, CD11b+, CD33+, two subsets can be subdivided from this population as either monocytic (CD14+) or granulocytic (CD15+) (Wesolowski et al., J Immunother Cancer (2013)1:10; Dumitru et al., Cancer Immunol Immunother (2012) 61: 1155-1167; Filipazzi et al., Cancer Immunol Immunother (2011) 61: 255-263). These cells have been demonstrated to be functionally immunosuppressive but their subtype and frequency is dependent on the disease being studied. Treatment of murine cancer models with gemcitabine shows a reduction in the total number of MDSCs (Suzuki et al., Clin Cancer Res (2005) 11: 6713-6721; Ding et al., Cancer Res (2014) 74(13): 3441-3453; Huang et al., Cancer Immunol Immunother (2013) 62: 1439-1451). The role of MDSC in EBV+ NPC is poorly understood.

SUMMARY OF THE INVENTION

In a first aspect, the present invention provides method for predicting whether a patient will be a long-term survivor on treatment of a disease by adoptive cell transfer (ACT), comprising:
  (i) analysing a blood-derived sample obtained from the patient for one or more prognostic markers of long-term survival on treatment of a disease by ACT, and;
  (ii) based on the analysis of step (i), predicting whether the patient will be a long-term survivor on treatment of the disease by ACT.

In some embodiments, the method comprises analysing the blood-derived sample for one or more correlates of the size and/or activity of effector immune cell and/or immunoregulatory immune cell populations.

In another aspect, the present invention provides a method of treating a patient by adoptive cell transfer (ACT), the method comprising:
  (i) analysing a blood-derived sample obtained from the patient for one or more prognostic markers of long-term survival on treatment of a disease by ACT;

(ii) based on the analysis of step (ii), predicting long-term survival of the patient by treatment of the disease by ACT; and
(iii) administering one or more doses of cells to the patient.

In another aspect, the present invention provides a method of selecting a patient for treatment of a disease by adoptive cell transfer (ACT), comprising:
(i) analysing a blood-derived sample obtained from the patient for one or more prognostic markers of long-term survival on treatment of a disease by ACT;
(ii) based on the analysis of step (i), predicting whether the patient will be a long-term survivor on treatment of the disease by ACT; and
(iii) selecting a patient predicted to be a long-term survivor on treatment of the disease by ACT for treatment of the disease by ACT.

In another aspect, the present invention provides a method of selecting a patient for continued treatment of a disease by adoptive cell transfer (ACT), comprising:
(i) analysing a blood-derived sample obtained from the patient for one or more prognostic markers of long-term survival on treatment of a disease by ACT;
(ii) based on the analysis of step (i), predicting whether the patient will be a long-term survivor on treatment of the disease by ACT; and
(iii) selecting a patient predicted to be a long-term survivor on treatment of the disease by ACT for continued treatment of the disease by ACT.

In some embodiments in accordance with various aspects of the present invention, the additionally comprises an initial step of administering a dose of cells to the patient. In some embodiments, the sample is obtained from the patient within a period of 4 weeks after administering the initial step of administering a dose of cells to the patient.

In some embodiments in accordance with various aspects of the present invention, the one or more prognostic markers comprise: a marker of myeloid-derived suppressor cell (MDSC) number or activity, a marker of regulatory T lymphocyte number or activity, and/or a marker of effector T lymphocyte number or activity.

In some embodiments in accordance with various aspects of the present invention, the one or more prognostic markers comprise: a marker of the amount of an infectious agent associated with the disease.

In some embodiments in accordance with various aspects of the present invention, analysing the blood-derived sample comprises determining one or more of: the level of interferon gamma (IFNγ), the level of CCL22, the level of IL-10, the level of IL-8, the level of CCL20 and the level of VEGF.

In some embodiments in accordance with various aspects of the present invention, analysing the blood-derived sample comprises:
(i) determining the ratio of the level of one or more markers of MDSC number or activity, or the level of one or more markers of regulatory T lymphocyte number or activity to the level of one or more markers of effector T lymphocyte number or activity, and/or
(ii) determining the ratio of the level of a marker of the amount of an infectious agent associated with the disease to the level of one or more markers of effector T lymphocyte number or activity.

In some embodiments, the method further comprises determining the relationship between the ratio of (i) and the ratio of (ii).

In some embodiments in accordance with various aspects of the present invention, analysing the blood-derived sample comprises: determining the level of IFNγ, determining the level of a nucleic acid of an infectious agent associated with the disease, determining the level of CXCL10, and/or determining the level of CCL20.

In some embodiments, a marker of MDSC number or activity and/or regulatory T lymphocyte number or activity is selected from the group consisting of: CXCL10, CCL20, number of MDSCs, the percentage of MDSCs as a proportion of live cells, the number of monocytes, the percentage of monocytes as a proportion of live cells, the percentage of monocytes as a proportion of the number of leukocytes, the percentage of FoxP3+ CTLA4+ regulatory T cells (Tregs) as a proportion of CD3+ cells, myeloid cell marker expression by peripheral blood mononuclear cells (PBMCs), and immune inhibitory factor expression by PBMCs.

In some embodiments, a marker of effector T lymphocyte number or activity is selected from the group consisting of: IFNγ, lymphocyte number, T lymphocyte number, the percentage of lymphocytes as a proportion of the number of leukocytes, the percentage of CD8+ cells as a proportion of the number of T lymphocytes, the percentage of CD4+ cells as a proportion of the number of T lymphocytes.

In some embodiments, a marker of the amount of an infectious agent associated with the disease is selected from the group consisting of: viral DNA, viral RNA, viral protein, viral envelope protein.

In some embodiments, in accordance with various aspects of the present invention, analysing the blood-derived sample comprises:
(i) determining the ratio of the level of IFNγ to the level of CXCL10 and/or CCL20,
(ii) determining the ratio of the level of a marker of the amount of an infectious agent associated with the disease to the level of IFNγ, and optionally
(iii) determining the relationship between the ratio of (i) and the ratio of (ii).

In a further aspect, the present invention provides a method of treatment of a disease by adoptive cell transfer (ACT), comprising administering to a patient one or more of: an agent for decreasing myeloid-derived suppressor cell (MDSC) number or activity, an agent for decreasing regulatory T cell number or activity, an agent for increasing effector T lymphocyte number or activity, and/or an agent for reducing the amount of an infectious agent associated with the disease.

In a related aspect, the present invention provides one or more of: an agent for decreasing myeloid-derived suppressor cell (MDSC) number or activity, an agent for decreasing regulatory T cell number or activity, an agent for increasing effector T lymphocyte number or activity, and/or an agent for reducing the amount of an infectious agent associated with the disease for use in a method of treatment of a disease by adoptive cell transfer (ACT).

In a further related aspect, the present invention provides the use of one or more of: an agent for decreasing myeloid-derived suppressor cell (MDSC) number or activity, an agent for decreasing regulatory T cell number or activity, an agent for increasing effector T lymphocyte number or activity, and/or an agent for reducing the amount of an infectious agent associated with the disease for use in the manufacture of a medicament for use in a method of treatment of a disease by adoptive cell transfer (ACT).

In some embodiments, in accordance with the various aspects, the one or more agents are administered to the patient prior to treatment by ACT. In some embodiments, the one or more agents are administered to the patient after a dose of cells has been administered to the patient.

In some embodiments, in accordance with the various aspects of the present invention the ACT comprises adoptive transfer of cytotoxic T lymphocytes (CTLs). In some embodiments, the CTLs are specific for a virus which causes or exacerbates the disease.

In some embodiments, in accordance with the various aspects of the present invention the disease is a cancer.

In some embodiments the CTLs are Epstein-Barr Virus (EBV)-specific CTLs. In some embodiments the CTLs are Human papillomavirus (HPV)-specific CTLs.

In some embodiments the cancer is nasopharyngeal carcinoma (NPC), optionally EBV-positive NPC. In some embodiments the cancer is cervical cancer, optionally HPV-positive cervical cancer.

In a further aspect, the present invention provides a kit comprising: means for detecting a marker of myeloid-derived suppressor cell (MDSC) number or activity and/or a marker of regulatory T lymphocyte number or activity and means for detecting a marker of effector T lymphocyte number or activity, optionally further comprising means for detecting a marker of the amount of an infectious agent associated with the disease.

The following paragraphs contain further statements describing the present invention:

The inventors demonstrate that the measurement of peripheral sera proteins, in EBV positive NPC patients undergoing CTL therapy after the first immunotherapy injection, can accurately identify one- and two-year survivors. Stratification of patients into one-year survivors can be achieved by measurement of eotaxin, MIP-3a (CCL20), and IFNγ, conversion of the measured values into ratios of IFNγ expression, and plotting the ratios against each other. Stratification of patients into two-year survivors can be achieved by measurement of EBV DNA, IP10 (CXCL10), and IFNγ, conversion of the measured values into ratios of IFNγ expression, and plotting the ratios against each other.

These parameters can be used to identify patients who will undergo successful therapy for the treatment of EBV-positive NPC by adoptive transfer of EBV-specific CTLs, and thus allow correct powering of downstream analysis.

The measurement of monocytic-MDSCs also forms the basis of a prognostic marker for CTL therapy. Measurement of this cell type can act as a marker for patient stratification.

These measurements can have use in other CTL immunotherapies against viral agents.

BRIEF DESCRIPTION OF THE FIGURES

Embodiments and experiments illustrating the principles of the invention will now be discussed with reference to the accompanying figures.

FIG. 2A Number of white blood cells, FIG. 2B Neutrophils as a percentage of leukocytes, FIG. 2C Lymphocytes as a percentage of leukocytes, and FIG. 2D Monocytes as a percentage of leukocytes.

FIG. 4A IFNγ, FIG. 4B EBV DNA, FIG. 4C CCL20, and FIG. 4D CCL10.

FIG. 7A CCL20:IFNγ vs. EBV DNA:IFNγ, and FIG. 7B CCL10:IFNγ vs. EBV DNA:IFNγ.

FIG. 9. Table 3 showing the results of statistical analysis of correlation of PBMC transcript level with overall survival at time point T1.

FIG. 10A CD68, FIG. 10B S100A8, and FIG. 10C LILRA5.

FIG. 11A Monocytes as a percentage of leukocytes, and FIG. 11B Monocytes as a percentage of the total number of live cells.

FIG. 12A Neutrophils as a percentage of leukocytes, and FIG. 12B Lymphocytes as a percentage of leukocytes.

FIG. 14A Mean+/−standard deviation for two year survivors and non-survivors, and FIG. 14B Individual data points for each patient.

FIGS. 18A-18C. Graphs showing level of RNA transcripts at T-1 (pre-chemotherapy) and T0 (post-chemotherapy) between. FIG. 18A NLRP3, FIG. 18B CD274 (PD-L1), and FIG. 18C STAT4.

FIG. 20A CD68, FIG. 20B LILRA5, and FIG. 20C S100A9.

FIG. 21. Table 4 showing the results of statistical analysis of correlation of PBMC transcript level with survival at time point T1.

FIG. 23. Table 5 showing the results of statistical analysis of correlation of PBMC transcript level with survival at time point T0.

DETAILED DESCRIPTION

Figure 1:
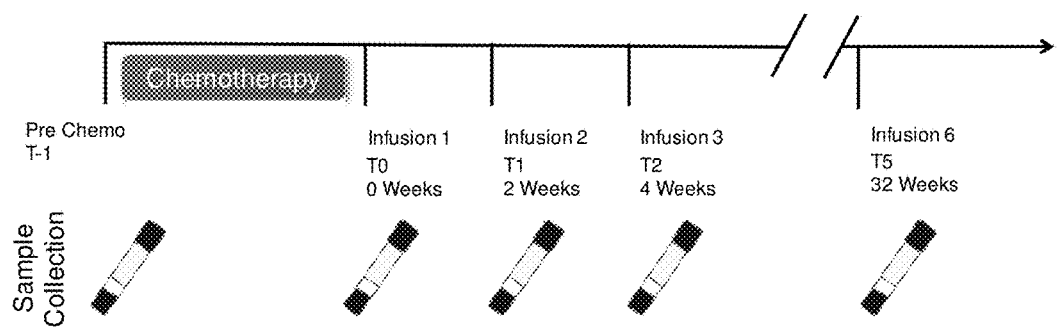
FIG. 1. Schematic showing the time points of sample collection throughout the Phase II clinical trial.

The present invention is broadly based on the finding that on the basis of analysis of patients' blood at different time points for correlates of the size and/or activity of the effector and immunoregulatory cell populations, it is possible to predict whether a patient will be a long-term survivor on treatment of the disease by adoptive cell transfer (ACT).

Adoptive Cell Transfer

The present invention relates to treatment of disease by adoptive cell transfer (ACT).

ACT involves the transfer of cells into a patient, the cells having therapeutic properties for the treatment of the disease. The cells transferred to the patient may be derived from the patient (i.e. autologous), or may be derived from a different subject (allogenic).

The cells may be immune cells. In some embodiments, the cells may be lymphocytes. In some embodiments, the cells may be T lymphocytes.

Adoptive cell transfer of T lymphocytes generally involves obtaining T cells from a subject, typically by drawing a blood sample from which T cells are isolated. The T cells are then typically treated or altered in some way, and then administered either to the same subject or to a different subject. Adoptive T cell transfer is typically aimed at providing a T cell population with certain desired characteristics to a subject, or increasing the frequency of T cells with such characteristics in that subject. Adoptive transfer of virus specific T cells is described, for example, in Cobbold et al., (2005) J. Exp. Med. 202: 379-386 and Rooney et al., (1998), Blood 92:1549-1555, hereby incorporated by reference in its entirety.

In some embodiments of the present invention the ACT comprises adoptive transfer of T cells, e.g. CD4+ or CD8+ T cells.

In some embodiments, the ACT comprises adoptive transfer of T cells which are specific for an infectious agent. In some embodiments, the T cells encode or express a T cell receptor (TCR) which is capable of recognising (i.e. binding to) a molecule derived form an infectious agent, e.g. in the context of presentation by an MHC molecule. In some embodiments, the infectious agent is an agent which is associated with the disease to be treated by the ACT. In some embodiments, the infectious agent causes or exacerbates the disease. The infectious agent may be e.g. a virus, bacteria, fungus, protozoa.

The virus for which the T cells are specific may be a dsDNA virus (e.g. adenovirus, herpesvirus, poxvirus), ssRNA virus (e.g. parvovirus), dsRNA virus (e.g. reovirus), (+)ssRNA virus (e.g. picornavirus, togavirus), (−)ssRNA virus (e.g. orthomyxovirus, rhabdovirus), ssRNA-RT virus (e.g. retrovirus) or dsDNA-RT virus (e.g. hepadnavirus). The present disclosure contemplates viruses of the families adenoviridae, herpesviridae, papillomaviridae, polyomaviridae, poxviridae, hepadnaviridae, parvoviridae, astroviridae, caliciviridae, picornaviridae, coronaviridae, flaviviridae, togaviridae, hepeviridae, retroviridae, orthomyxoviridae, arenaviridae, bunyaviridae, filoviridae, paramyxoviridae, rhabdoviridae and reoviridae.

Viruses associated with a disease or disorder are of particular interest. Accordingly, the following viruses are contemplated: adenovirus, Herpes simplex type 1 virus, Herpes simplex type 2 virus, Varicella-zoster virus, Epstein-Barr virus, Human cytomegalovirus, Human herpesvirus type 8, Human papillomavirus, BK virus, JC virus, Smallpox, Hepatitis B virus, Parvovirus B19, Human Astrovirus, Norwalk virus, coxsackievirus, hepatitis A virus, poliovirus, rhinovirus, severe acute respiratory syndrome virus, hepatitis C virus, yellow fever virus, dengue virus, West Nile virus, TBE virus, Rubella virus, Hepatitis E virus, Human immunodeficiency virus, influenza virus, lassa virus, Crimean-Congo hemorrhagic fever virus, Hantaan virus, ebola virus, Marburg virus, measles virus, mumps virus, parainfluenza virus, respiratory syncytial virus, rabies virus, hepatitis D virus, rotavirus, orbivirus, coltivirus, and banna virus.

In some embodiments, the virus is Epstein-Barr virus (EBV). Accordingly, in some embodiments the ACT is of EBV-specific T cells (e.g. EBV-specific CTLs). In some embodiments, the EBV is strain B95-8, P3HR-1, or a derivative thereof.

In some embodiments, the virus is Human papillomavirus (HPV). Accordingly, in some embodiments the ACT is of HPV-specific T cells (e.g. HPV-specific CTLs). In some embodiments, the HPV is HPV16 or HPV18 or a derivative thereof.

In some embodiments, the T cells are cytotoxic T lymphocytes (CTLs). CTLs are capable of effecting cell death in cells infected with a virus by releasing cytotoxic factors including perforin, granzymes, granulysin, and/or by inducing apoptosis of the infected cell by ligating FAS on the infected cell through FASL expressed on the T cell (described for example by Chavez-Galan et al., Cellular and Molecular Immunology (2009) 6(1): 15-25, hereby incorporated by reference in its entirety). Cytotoxicity can be investigated, for example, using any of the methods reviewed in Zaritskaya et al., Expert Rev Vaccines (2011), 9(6):601-616, hereby incorporated by reference in its entirety. One example of an assay for cytotoxicity of a T cell for to a target cell is the $^{51}$Cr release assay, in which target cells are treated with $^{51}$Cr, which they internalise. Lysis of the target cells by T cells results in the release of the radioactive $^{51}$Cr into the cell culture supernatant, which can be detected.

In some embodiments, the ACT is of EBV-specific CTLs. In some embodiments, the ACT is of HPV-specific CTLs.

Disease to be Treated

The disease to be treated by the ACT may be any disease for which the ACT is a therapeutic treatment.

In some embodiments the disease is a disease which is associated with (e.g. caused or exacerbated by) infection with an infectious agent, e.g. an infectious agent described herein. In some embodiments the disease may be a disease which is caused or exacerbated by infection with a virus, e.g. a virus described herein.

In some embodiments the disease may be a disease which is associated with (e.g. caused or exacerbated by) infection with EBV. Diseases associated with and/or caused/exacerbated by EBV infection are described in Taylor et al., Ann Rev Immunol (2015) 33:787-821 and include nasopharyngeal carcinoma, infectious mononucleosis, Burkitt's lymphoma, Hodgkin's lymphoma, gastric cancer, multiple sclerosis, lymphomatoid granulomatosis, Gianotti-Crosti syndrome, erythema multiforme, acute genital ulcers, oral hairy leukoplakia, and disorders related to alpha-synuclein aggregation (e.g. Parkinson's disease, dementia with Lewy bodies and multiple system atrophy).

In some embodiments, the disease may be a cancer. In some embodiments, the cancer may be an EBV-positive cancer. A cancer can be determined to be an EBV-positive cancer by any suitable means, which are well known to the skilled person.

In some embodiments the cancer is nasopharyngeal carcinoma. In some embodiments the disease is EBV-positive nasopharyngeal carcinoma.

In some embodiments the cancer is hepatic cancer/liver cancer (e.g. hepatocellular carcinoma, hepatoblastoma). In some embodiments the disease is EBV-positive hepatic cancer/liver cancer.

In some embodiments the cancer is lung cancer (e.g. non-small cell lung cancer (NSCLC)). In some embodiments the disease is EBV-positive lung cancer.

In some embodiments the cancer is gastric cancer (e.g. non-small cell lung cancer (NSCLC)). In some embodiments the disease is EBV-positive gastric cancer.

In some embodiments the disease may be a disease which is associated with (e.g. caused or exacerbated by) infection with HPV.

Human papillomavirus (HPV) is a DNA virus that establishes productive infections in keratinocytes of the skin or mucous membranes. There are over 170 types of HPV, a subset of which HPV types are carcinogenic, including high-risk sexually transmitted types that can develop into genital neoplasias, including cervical intraepithelial neoplasia (CIN), vulvar intraepithelial neoplasia (VIN), penile intraepithelial neoplasia (PIN), and/or anal intraepithelial neoplasia (AIN), for example. HPV-induced cancers arise when viral sequences are integrated into the cellular DNA of host cellst cells. Some of the HPV "early" genes, such as E6 and E7, act as oncogenes that promote tumor growth and malignant transformation.

Diseases associated with and/or caused/exacerbated by HPV infection are described in Doorbar et al. Rev Med Virol (2016); 25: 2-23, and include *Condyloma acuminatum*, focal epithelia hyperplasia, cervical neoplasia, anogenital cancers (e.g. cervical cancer (e.g. cervical intraepithelial neoplasia (CIN), LSIL), e.g keratinizing SCC, e.g. of the vulva (e.g. vulvar intraepithelial neoplasia (VIN)), vagina, penis (penile intraepithelial neoplasia (PIN)), anus (anal intraepithelial neoplasia (AIN))), oral papilloma and head and neck cancer (e.g. of the oropharynx (e.g. oropharyngeal carcinoma), head and neck squamous cell carcinoma (HNSCC)).

In some embodiments, the disease may be a cancer. In some embodiments, the cancer may be an HPV-positive cancer, e.g. a HPV16- or HPV18-positive. A cancer can be determined to be an HPV-positive cancer by any suitable means, which are well known to the skilled person.

In some embodiments, the cancer is an anogenital cancer. In some embodiments the disease is a HPV-positive anogenital cancer. In some embodiments the cancer is cervical cancer. In some embodiments the disease is HPV-positive cervical cancer.

In some embodiments the cancer is a head and neck cancer. In some embodiments the disease is a HPV-positive head and neck cancer. In some embodiments the cancer is oropharyngeal cancer. In some embodiments the disease is a HPV-positive oropharyngeal cancer. In some embodiments the cancer is HNSCC. In some embodiments the disease is a HPV-positive HNSCC.

The cancer may be any unwanted cell proliferation (or any disease manifesting itself by unwanted cell proliferation), neoplasm or tumor or increased risk of or predisposition to the unwanted cell proliferation, neoplasm or tumor. The cancer may be benign or malignant and may be primary or secondary (metastatic). A neoplasm or tumor may be any abnormal growth or proliferation of cells and may be located in any tissue. Examples of tissues include the adrenal gland, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node, lymphoblast, maxilla, mediastinum, mesentery, myometrium, nasopharynx, omentum, oral cavity, ovary, pancreas, parotid gland, peripheral nervous system, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells.

Samples

The present invention involves analysing a sample for one or more prognostic markers of survival on treatment by ACT.

The sample is obtained from a patient, and may be e.g. a blood or tissue sample. In some embodiments, the sample is a blood or blood-derived sample. That is, the sample may be whole blood obtained from the patient, or may be derived from a quantity of blood obtained from the patient. In some embodiments, a blood derived sample may be quantity of blood plasma or serum derived from the subject's blood. This may comprise the fluid portion of the blood obtained after removal of the fibrin clot and blood cells. The sample may be a preparation of cells obtained from the blood sample (e.g. nucleated cells, PBMCs etc.).

In some embodiments, the sample has been obtained from the subject. In some embodiments, the method is performed in vitro. In some embodiments, the methods are not practised on the human or animal body.

In some embodiments, the methods comprise a step of obtaining a sample from the subject. In some embodiments, the sample may be obtained and then stored, e.g. at −80° C. The stored sample can be thawed and analysed in accordance with the methods of the invention.

In some embodiments, a sample is obtained from the patient at a pre-determined time point in relation to a proposed or contemporaneous course of treatment of the disease. In some embodiments, samples are obtained from the patient at more than one time point in relation to a proposed or contemporaneous course of treatment of the disease.

In some embodiments, the sample is or has been obtained from the patient prior to a therapeutic intervention to treat the disease. A therapeutic intervention to treat the disease may be e.g. chemotherapy, immunotherapy, radiotherapy, surgery, vaccination and/or hormone therapy. A therapeutic intervention to treat the disease may be ACT, e.g. adoptive transfer of CTLs, e.g. CTLs specific for an infectious agent which causes or exacerbates the disease.

In some embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year prior to a therapeutic intervention to treat the disease. In some embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day prior to a therapeutic intervention to treat the disease.

In some embodiments, the sample is or has been obtained from the patient during the course of a therapeutic intervention to treat the disease. In some embodiments, the sample is or has been obtained from the patient after commencement of a therapeutic intervention to treat the disease.

In some embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year after a therapeutic intervention to treat the disease (preferably after commencement, i.e. first administration of, the therapeutic intervention). In some embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day after a therapeutic intervention to treat the disease (preferably after commencement, i.e. first administration of, the therapeutic intervention).

In some embodiments, the sample is or has been obtained from the patient on or after completion of the course of a therapeutic intervention to treat the disease, e.g. on or after completion of a course of chemotherapy or radiotherapy. In some embodiments chemotherapy comprises treatment with gemcitabine and/or carboplatin.

In some embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year after completion of the course of a therapeutic intervention to treat the disease. In some embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day after completion of the course of a therapeutic intervention to treat the disease.

In some embodiments, the sample is or has been obtained from the patient prior to administration of cells to the patient. In some particular embodiments, the sample is or has been obtained from the patient prior to the commencement of treatment of the patient by ACT.

In some embodiments the sample is or has been obtained from the patient after cells have been administered to the patient. In some embodiments the sample is or has been obtained after cells have been administered to a patient in accordance with a method of treatment of the disease by ACT. In some embodiments the sample is or has been obtained after cells have been administered to a patient in accordance with a screening step to determine whether the patient would be a long-term survivor on treatment of the disease by ACT.

As used herein, 'long-term survival' means survival on treatment of the disease by ACT of a period of greater than 6 months, e.g. survival for a period of greater than 6, 7, 8, 10, 11, 12, 13, 14, 15, 16, 17, 18, 19, 20, 21, 22, 23, 24, 25, 26, 27, 28, 29, 30, 31, 32, 33, 34, 35, or 36 months. In some embodiments, long-term survival may be classed as survival for one of at least 12 months, at least 18 months, at least 24 months, or at last 26 months. In some embodiments, long-term survival may be classed as survival for at least 24 months.

Survival 'on treatment' by ACT means survival during the course of treatment by administration of cells in accordance with a method of treating a disease by ACT, e.g. as described herein. A period of survival of a patient on treatment with ACT may be measured from the date of administration, e.g. first administration, of a therapy to the patient, e.g. administration of a dose of cells by ACT.

'Increased' survival as used herein refers to survival for a period of time which is greater (i.e. a longer period of time) relative to a reference period of time of survival. The reference period may e.g. be the average (e.g. the mean, median or mode) survival period for a patient on treatment by ACT, or the survival period for a patient who is not a long-term survivor on treatment of the disease by ACT.

In some embodiments, the sample is or has been obtained from the patient after administration of a single dose of cells. In some embodiments the sample is or has been obtained after administration of more than one dose of cells, e.g. after 2, 3, 4, 5, 6, 7, 8, 9, or 10 doses of cells have been administered to the patient.

In some embodiments the sample is or has been obtained from the patient within a defined period of time after cells have been administered to the patient. In some embodiments the sample is or has been obtained from the patient up to 1 day, 2 days, 3 days, 4 days, 5 days, 6 days, 7 days, 8 days, 9 days, 10 days, 11 days, 12 days, 13 days, 2 weeks, 3 weeks, 4 weeks, 2 months, 3 months, 4 months, 5 months, 6 months or 1 year after cells have been administered to the patient. In some embodiments the sample is or has been obtained from the patient not more than 1 year, 6 months, 5 months, 4 months, 3 months, 2 months, 4 weeks, 3 weeks, 2 weeks, 13 days, 12 days, 11 days, 10 days, 9 days, 8 days, 7 days, 6 days, 5 days, 4 days, 3 days, 2 days or 1 day after cells have been administered to the patient.

In some embodiments the sample is or has been obtained from the patient between 1 day to 6 weeks, 1 day to 4 weeks, 5 days to 3 weeks, or 1 week to 2 weeks after cells have been administered to the patient.

In some embodiments, the methods may comprise analysis of samples obtained at different time points. For example, in some embodiments the methods may comprise analysis of a sample obtained prior to therapeutic intervention to treat a disease, and analysis after therapeutic intervention to treat a disease.

Analysis of Prognostic Markers

The methods of the present invention involve analysing a sample for one or more prognostic markers.

The method may be performed in vitro or ex vivo. In some embodiments the method is not performed on the human or animal body.

The methods comprise analysing blood-derived sample(s) for one or more correlates of the size and/or activity of effector immune cell and/or immunoregulatory immune cell populations.

In some embodiments, the analysis comprises determining the presence of, or level (i.e. the amount) of, a given marker. In some embodiments the analysis comprises measuring the level of or quantifying the marker.

In some embodiments the method comprises determining the presence/absence or measuring the level of (e.g. the amount) of a given molecule in a sample. In some embodiments, the molecule may be a nucleic acid (e.g. DNA, RNA), protein, peptide, carbohydrate (e.g. a sugar) or lipid.

In some embodiments, the level of a protein may be determined by analysing the blood-derived sample for nucleic acid encoding the protein. In some embodiments, the level of a protein may be determined by analysing the blood-derived sample for the protein or a fragment thereof. In some embodiments, the level of a protein may be determined by analysing the blood-derived sample for a correlate of the presence/activity of the protein.

In some embodiments, the number of a given cell type may be determined by analysing the blood-derived sample for the expression of a marker or plurality of markers (e.g. nucleic acid/protein/peptide marker(s)) for that cell type. In some embodiments, the number of a given cell type may be determined by analysing the blood-derived sample for a correlate of the presence/activity of that cell type.

Nucleic acids can be detected and/or measured by various means known to those skilled in the art. For example, gene expression can be analysed by measuring levels of mRNA by quantitative real-time PCR (qRT-PCR), nanostring analysis etc. RNA/DNA of a pathogen can be measured e.g. by qPCR.

Proteins can be detected and/or measured by various methods well known in the art, e.g. by antibody-based methods, for example by western blot, immunohistochemistry, immunocytochemistry, flow cytometry, ELISA, ELISPOT, reporter-based methods, etc.

A given activity, e.g. an activity associated with a given cell type, can be measured e.g. by an assay (e.g. an in vitro assay) for that activity. In some embodiments, an activity can be measured by analysing a sample for a correlate of the activity, e.g. for a nucleic acid, protein or fragment thereof associated with the activity. By way of example, the level of IFNγ protein or RNA/DNA encoding IFNγ is a correlate of effector T lymphocyte (e.g. CTL) activity.

In some embodiments, the method comprises detecting the presence of, or determining the number or proportion of (which may e.g. be expressed as a percentage), a given cell type or class of cells in the sample. This can be achieved by a variety of methods including analysis of cells obtained from the sample by flow cytometry, e.g. after labelling of the cells with antibodies specific for markers allowing differentiation of cell types.

The inventors have identified a plurality of markers which are positively or negatively associated with survival of a patient on treatment of a disease by ACT, summarised in Table A.

For the avoidance of any doubt, a 'positive' association in Table A below indicates that an higher number/level/percentage is associated with increased and/or long-term survival of a patient on treatment of the disease by ACT. A 'negative' association in Table A below indicates that a lower number/level/percentage is associated with increased and/or long-term survival of a patient on treatment of the disease by ACT.

TABLE A

| Marker | Positive/negative association with survival on treatment of a disease by ACT |
| --- | --- |
| Number of myeloid-derived suppressor cell (MDSCs) | Negative |
| MDSC activity | Negative |
| Number of regulatory T lymphocytes | Negative |
| Regulatory T lymphocyte activity | Negative |
| Number of lymphocytes | Positive |
| Percentage of lymphocytes as a proportion of the number of leukocytes | Positive |
| Number of effector T lymphocytes | Positive |
| Effector T lymphocyte activity | Positive |
| Amount of an infectious agent associated with the disease | Negative |
| CXCL10 | Negative |
| CCL20 | Negative |
| CCL22 | Negative |

TABLE A-continued

| Marker | Positive/negative association with survival on treatment of a disease by ACT |
| --- | --- |
| IL-10 | Negative |
| IL-8 | Negative |
| VEGF | Negative |
| Nucleic acid of an infectious agent associated with the disease | Negative |
| IFNγ | Positive |
| Number of leukocytes | Positive |
| Number of neutrophils | Negative |
| Percentage of neutrophils as a proportion of the number of leukocytes | Negative |
| Number of monocytes | Negative |
| Percentage of monocytes as a proportion of the number of leukocytes | Negative |
| Percentage of CD8+ cells as a proportion of the number of T lymphocytes | Positive |
| Percentage of CD4+ cells as a proportion of the number of T lymphocytes | Positive |
| Percentage of monocytes as a proportion of live cells | Negative |
| Percentage of MDSCs as a proportion of live cells | Negative |
| Percentage of FoxP3+ CTLA4+ regulatory T cells (Tregs) as a proportion of CD3+ cells | Negative |
| Expression of myeloid cell markers by peripheral blood mononuclear cells (PBMCs) | Negative |
| Expression of immune inhibitory factors by PBMCs | Negative |

Accordingly, in some embodiments of the present invention the one or more prognostic markers of long-term survival on treatment of a disease by ACT comprise:
(a) a marker of MDSC number;
(b) a marker of MDSC activity;
(c) a marker of regulatory T lymphocyte number;
(d) a marker of regulatory T lymphocyte activity;
(e) a marker of lymphocyte number;
(f) the percentage of lymphocytes as a proportion of the number of leukocytes;
(g) a marker of effector T lymphocyte number;
(h) a marker of effector T lymphocyte activity;
(i) a marker of the amount of an infectious agent associated with the disease;
(j) the level of CXCL10;
(k) the level of CCL20;
(l) the level of CCL22;
(m) the level of IL-10;
(n) the level of IL-8;
(o) the level of VEGF;
(p) the level of nucleic acid of an infectious agent associated with the disease;
(q) the level of IFNγ;
(r) the number of leukocytes;
(s) the number of neutrophils;
(t) the percentage of neutrophils as a proportion of the number of leukocytes;
(u) the number of monocytes;
(v) the percentage of monocytes as a proportion of the number of leukocytes;
(w) the percentage of CD8+ cells as a proportion of the number of T lymphocytes;
(x) the percentage of CD4+ cells as a proportion of the number of T lymphocytes;
(y) the percentage of monocytes as a proportion of live cells;

(z) the percentage of myeloid derived suppressor cells (MDSCs) as a proportion of live cells;
(aa) the percentage of FoxP3+ CTLA4+ regulatory T cells (Tregs) as a proportion of CD3+ cells;
(bb) the level of expression of one or more myeloid cell markers by peripheral blood mononuclear cells (PBMCs); and/or
(cc) the level of expression of one or more immune inhibitory factors by PBMCs.

In some embodiments, the methods comprise analysing a blood-derived sample obtained from a patient for 1, 2, 3, 4, 5, 6, 7, 8, 9, 10, 11, 12, 13, 14, 15, 16, 17, 18, or 19 prognostic markers of long-term survival on treatment of a disease by ACT.

In some embodiments of the present invention, analysing the blood-derived sample comprises one or more of:
(a) determining myeloid-derived suppressor cell (MDSC) number;
(b) determining the level of myeloid-derived suppressor cell (MDSC) activity;
(c) determining the regulatory T lymphocyte number;
(d) determining the level of regulatory T lymphocyte activity;
(e) determining lymphocyte number;
(f) determining the percentage of lymphocytes as a proportion of the number of leukocytes;
(g) determining effector T lymphocyte number;
(h) determining the level of effector T lymphocyte activity;
(i) determining the amount of an infectious agent associated with the disease;
(j) determining the level of CXCL10;
(k) determining the level of CCL20;
(l) determining the level of CCL22;
(m) determining the level of IL-10;
(n) determining the level of IL-8;
(o) determining the level of VEGF;
(p) determining the level of nucleic acid of an infectious agent associated with the disease;
(q) determining the level of IFNγ;
(r) determining the number of leukocytes;
(s) determining the number of neutrophils;
(t) determining the percentage of neutrophils as a proportion of the number of leukocytes;
(u) determining the number of monocytes;
(v) determining the percentage of monocytes as a proportion of the number of leukocytes;
(w) determining the percentage of CD8+ cells as a proportion of the number of T lymphocytes;
(x) determining the percentage of CD4+ cells as a proportion of the number of T lymphocytes;
(y) determining the percentage of monocytes as a proportion of live cells;
(z) determining the percentage of myeloid derived suppressor cells (MDSCs) as a proportion of live cells;
(aa) determining the percentage of FoxP3+ CTLA4+ regulatory T cells (Tregs) as a proportion of CD3+ cells;
(bb) determining the level of expression of one or more myeloid cell markers by peripheral blood mononuclear cells (PBMCs); and/or
(cc) determining the level of expression of one or more immune inhibitory factors by PBMCs.

In some embodiments, the one or more prognostic markers comprise: a marker of myeloid-derived suppressor cell (MDSC) number or activity, a marker of regulatory T lymphocyte number or activity, and/or a marker of effector T lymphocyte number or activity. In some embodiments, the one or more prognostic markers comprise: a marker of the amount of an infectious agent associated with the disease.

MDSC number or activity may be determined by analysis of one or more properties of MDSCs described, for example, in Greten et al., Int. Immunopharmacol (2011) 11:802-807, and Gabrilovich and Nagaraj, Nat Rev Immunol (2009) 9:162-174, both hereby incorporated by reference in their entirety. In some embodiments, MDSCs may be identified by reference to one or more of the following surface markers: CD33+, CD11b+, CD14+, CD16−, CD15−, HLADR$^{low}$.

In some embodiments, a marker of myeloid-derived suppressor cell (MDSC) number or activity, or a marker of regulatory T lymphocyte number or activity, may be selected from the group consisting of: CXCL10, CCL20, CCL22, IL-10, IL-8, number of MDSCs, the percentage of MDSCs as a proportion of live cells, the number of monocytes, the percentage of monocytes as a proportion of live cells, the percentage of monocytes as a proportion of the number of leukocytes, myeloid cell marker expression by peripheral blood mononuclear cells (PBMCs), immune inhibitory factor expression by PBMCs and the percentage of FoxP3+ CTLA4+ regulatory T cells (Tregs) as a proportion of CD3+ cells.

In some embodiments, a myeloid cell marker and/or an immune inhibitory factor/marker according to the present invention may be selected from Table 3 (FIG. 9). In some embodiments, the myeloid cell marker and/or an immune inhibitory factor/marker may be selected from one or more of CD68, LILRA5, S100A8, S100A9, S100A12, LILRB4, MSR1, CXCL16, CLEC7A and TREM1. In some embodiments, the myeloid cell marker and/or an immune inhibitory factor/marker may be selected from one or more of CD68, LILRA5, S100A8 and S100A9.

In some embodiments, a myeloid cell marker and/or an immune inhibitory factor/marker may be selected from one or more of NLRP3, PD-L1 and STAT4.

In some embodiments, a myeloid cell marker and/or an immune inhibitory factor/marker according to the present invention may be selected from one or more of IL-10, CCL22, IL-IL-8, VEGF and CCL20.

T lymphocyte number or activity may be determined by analysis of one or more properties of T lymphocytes which are well known to the skilled person. T lymphocyte markers include CD3 polypeptides (e.g. CD3γ CD3ε CD3ζ or CD3δ), TCR polypeptides (TCRα or TCRβ), CD27, CD28, CD4 and CD8.

As used herein, a 'regulatory T lymphocyte' refers to a T lymphocyte having immunomodulatory activity. Regulatory T lymphocytes (Tregs) generally suppress/downregulate induction, proliferation and/or function of effector T cells. Treg phenotype and function is reviewed by Vignali et al., Nat Rev Immunol (2008) 8(7):523-532, which is hereby incorporated by reference in its entirety. Markers of Tregs include FoxP3 and CTLA4 expression.

As used herein, an 'effector T lymphocyte' refers to T lymphocytes having an effector function. Examples of effector T lymphocytes (Teffs) include T helper cells, cytotoxic T lymphocytes (CTLs) and memory T cells. Teff phenotype and function is reviewed in Janeway, Immunobiology: The Immune System in Health and Disease; 5$^{th}$ Edn. 2001, at chapter 8 (hereby incorporated by reference in its entirety).

In some embodiments, a marker of effector T cell number or activity may be selected from the group consisting of: IFNγ, lymphocyte number, T lymphocyte number, the percentage of lymphocytes as a proportion of the number of leukocytes, effector T lymphocyte number, the percentage of CD8+ cells as a proportion of the number of T lymphocytes, and the percentage of CD4+ cells as a proportion of the number of T lymphocytes.

The amount of an infectious agent associated with the disease can be determined by analysis e.g. of the amount of a marker of the infectious agent. For example, a marker of the infectious agent may be a nucleic acid (e.g. RNA or DNA) of the infectious agent or a protein/peptide of the infectious agent. In some embodiments, a marker of the amount of an infectious agent associated with the disease is selected from the group consisting of: viral DNA (e.g. viral genomic DNA), viral RNA (e.g. viral genomic RNA), viral protein, and viral envelope protein.

In some embodiments, analysing the blood-derived sample comprises: determining the level of IFNγ, determining the level of a nucleic acid of an infectious agent associated with the disease, determining the level of CXCL10, and/or determining the level of CCL20.

In some embodiments, analysing the blood-derived sample comprises determining one or more ratios between the determined levels of prognostic markers of long-term survival on treatment of a disease by ACT. Levels and/or ratios may be transformed (e.g. $\log_{10}$ or $\log_e$ transformed) to assist the analysis.

In some embodiments, the analysis comprises determining the ratio of the level of a marker of the amount of an infectious agent associated with the disease to the level of one or more markers of MSDC number or activity and/or one or more markers of regulatory T lymphocyte number or activity, and/or determining the ratio of the level of a marker of the amount of an infectious agent associated with the disease to the level of one or more markers of effector T lymphocyte number or activity.

In some embodiments, the analysis comprises determining the ratio of the level of one or more molecules derived from an infectious agent associated with the disease to the level of one or more factors produced by MDSCs and/or one or more factors produced by regulatory T lymphocytes, and/or determining the ratio of the level of one or more molecules derived from an infectious agent associated with the disease to the level of one or more factors produced by effector T lymphocytes.

In some embodiments, analysing the blood-derived sample comprises: determining the ratio of the level of CCL20 to the level of IFNγ, determining the ratio of the level of CXCL10 to the level of IFNγ, and/or determining the ratio of the level of a nucleic acid of an infectious agent associated with the disease to the level of IFNγ.

In some embodiments of the methods of the present invention, analysing the blood-derived sample comprises comparing the determined level/number/percentage of one or more prognostic markers of long-term survival to reference value(s) for the marker. In some embodiments, the reference value is a value for that marker which is indicative of long-term survival or non-survival of a patient on treatment of a disease by ACT.

In some embodiments the reference value is the value for that marker in a comparable sample obtained from a subject of interest. In some embodiments, the subject is a healthy control individual. In some embodiments the subject is patient having the disease. In some embodiments the subject is a patient surviving for a longer than average (e.g. median or mean, mode) amount of time on treatment of the disease by ACT (i.e. a patient surviving for a longer amount of time than the average survival of a patient on treatment of the disease by ACT). In some embodiments the subject is a long-term survivor on treatment of the disease by ACT. In some embodiments the subject is a patient surviving for a shorter than average amount of time on treatment of the disease by ACT (i.e. a patient surviving for a shorter amount of time than the average survival of a patient on treatment of the disease by ACT). In some embodiments the subject is not a long-term survivor on treatment of the disease by ACT.

In some embodiments the value may be an average (e.g. mean, median, mode) value for the marker for a plurality of subjects, e.g. a plurality of subjects according to an embodiment of the preceding paragraph.

In some embodiments, determination of one or more of the following in relation to a reference value for a patient surviving for shorter than the average amount of time on treatment of the disease by ACT, a patient who is not a long-term survivor on treatment of the disease by ACT, or a patient surviving for the average amount of time on treatment of the disease by ACT may be predictive of increased and/or long-term survival on treatment of the disease by ACT:

(1) lower number of MDSCs;
(2) lower MDSC activity;
(3) lower number of regulatory T lymphocytes;
(4) lower regulatory T lymphocyte activity;
(5) greater number of lymphocytes;
(6) greater percentage of lymphocytes as a proportion of the number of leukocytes;
(7) greater number of effector T lymphocytes;
(8) greater effector T lymphocyte activity;
(9) lower amount of an infectious agent associated with the disease;
(10) lower CXCL10;
(11) lower CCL20;
(12) lower CCL22;
(13) lower IL-10;
(14) lower IL-8;
(15) lower VEGF;
(16) lower amount of nucleic acid of an infectious agent associated with the disease;
(17) greater IFNγ;
(18) greater number of leukocytes;
(19) lower number of neutrophils;
(20) lower percentage of neutrophils as a proportion of the number of leukocytes;
(21) lower number of monocytes;
(22) lower percentage of monocytes as a proportion of the number of leukocytes;
(23) greater percentage of CD8+ cells as a proportion of the number of T lymphocytes;
(24) greater percentage of CD4+ cells as a proportion of the number of T lymphocytes;
(25) lower percentage of monocytes as a proportion of the number of live cells;
(26) lower percentage of MDSCs as a proportion of the number of live cells;
(27) lower percentage of FoxP3+ CTLA4+ Tregs as a proportion of the number of CD3+ cells;
(28) lower level of expression of one or more myeloid cell markers by PBMCs; and/or
(29) lower level of expression of one or more immune inhibitory factors by PBMCs.

In some embodiments, determination of one or more of the following in relation to a reference value for a patient surviving for longer than the average amount of time on treatment of the disease by ACT, or a long-term survivor on treatment of the disease by ACT, may be predictive of increased and/or long-term survival on treatment of the disease by ACT:
(1) comparable or lower number of MDSCs;
(2) comparable or lower MDSC activity;
(3) comparable or lower number of regulatory T lymphocytes;
(4) comparable or lower regulatory T lymphocyte activity;
(5) comparable or greater number of lymphocytes;
(6) comparable or greater number of lymphocytes as a proportion of the number of leukocytes;
(7) comparable or greater number of effector T lymphocytes;
(8) comparable or greater effector T lymphocyte activity;
(9) comparable or lower amount of an infectious agent associated with the disease;
(10) comparable or lower CXCL10;
(11) comparable or lower CCL20;
(12) comparable or lower CCL22;
(13) comparable or lower IL-10;
(14) comparable or lower IL-8;
(15) comparable or lower VEGF;
(16) comparable or lower amount of nucleic acid of an infectious agent associated with the disease;
(17) comparable or greater IFNγ;
(18) comparable or greater number of leukocytes;
(19) comparable or lower number of neutrophils;
(20) comparable or lower percentage of neutrophils as a proportion of the number of leukocytes;
(21) comparable or lower number of monocytes;
(22) comparable or lower percentage of monocytes as a proportion of the number of leukocytes;
(23) comparable or greater percentage of CD8+ cells as a proportion of the number of T lymphocytes;
(24) comparable or greater percentage of CD4+ cells as a proportion of the number of T lymphocytes;
(25) comparable or lower percentage of monocytes as a proportion of the number of live cells;
(26) comparable or lower percentage of MDSCs as a proportion of the number of live cells;
(27) comparable or lower percentage of FoxP3+ CTLA4+ Tregs as a proportion of the number of CD3+ cells;
(28) comparable or lower level of expression of one or more myeloid cell markers by PBMCs; and/or
(29) comparable or lower level of expression of one or more immune inhibitory factors by PBMCs.

In some embodiments, the sample for such analysis is/has been obtained from a patient after a dose (e.g. a first dose) of cells have been administered to the patient by ACT, e.g. within 4 weeks of administration of the cells. In some embodiments, the sample for such analysis is/has been obtained from a patient prior to a therapeutic intervention (e.g. chemotherapy and/or ACT) to treat the disease. In some embodiments, the sample for such analysis is/has been obtained from a patient after completion of a therapeutic intervention (e.g. chemotherapy) to treat the disease, and prior to administration of cells to the patient.

In some embodiments, a lower level/number/percentage as compared to a reference value is one of less than 1 times, less than 0.95 times, less than 0.9 times, less than 0.85 times, less than 0.8 times, less than 0.75 times, less than 0.7 times, less than 0.65 times, less than 0.6 times, less than 0.55 times, less than 0.5 times, less than 0.45 times, less than 0.4 times, less than 0.35 times, less than 0.3 times, less than 0.25 times, less than 0.2 less than 0.15 times, or less than 0.1 times the level/number/percentage of the reference value.

In some embodiments, a greater level/number/percentage as compared to a reference value is one of more than 1 times, more than 1.1 times, more than 1.2 times, more than 1.3 times, more than 1.4 times, more than 1.5 times, more than 1.6 times, more than 1.7 times, more than 1.8 times, more than 1.9 times, more than 2 times, more than 2.1 times, more than 2.2 times, more than 2.3 times, more than 2.4 times, more than 2.5 times, more than 2.6 times, more than 2.7 times, more than 2.8 times, more than 2.9 times, more than 3 times, more than 3.1 times, more than 3.2 times, more than 3.3 times, more than 3.4 times, more than 3.5 times, more than 3.6 times, more than 3.7 times, more than 3.8 times, more than 3.9 times, more than 4 times, more than 4.1 times, more than 4.2 times, more than 4.3 times, more than 4.4 times, more than 4.5 times, more than 4.6 times, more than 4.7 times, more than 4.8 times, more than 4.9 times, or more than 5 times the level/number/percentage of the reference value.

In some embodiments, a number of leukocytes of one of about $7 \times 10^9/L$, $6.5 \times 10^9/L$, $6 \times 10^9/L$, $5.5 \times 10^9/L$, $5 \times 10^9/L$, $4.5 \times 10^9/L$, $4 \times 10^9/L$ or lower is predictive of increased and/or long-term survival. In some embodiments, the sample for such analysis is/has been obtained from a patient after a dose (e.g. a first dose) of cells have been administered to the patient by ACT, e.g. within 4 weeks of administration of the cells.

In some embodiments, a percentage of neutrophils as a proportion of leukocytes one of about 70%, 65%, 60%, 55%, 50%, 45%, 40% or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a percentage of lymphocytes as a proportion of leukocytes of one of about 10%, 15%, 20%, 25%, 30%, 35%, 40% or higher is predictive of increased and/or long-term survival, e.g. in a sample obtained from a patient after a dose (e.g. a first dose) of cells have been administered to the patient by ACT, e.g. within 4 weeks of administration of the cells.

In some embodiments, a log 10 transformed level of IFNγ of one of about 0.25 pg/ml, 0.3 pg/ml, 0.35 pg/ml, 0.4 pg/ml, 0.45 pg/ml, 0.5 pg/ml, 0.55 pg/ml, 0.6 pg/ml, 0.65 pg/ml, 0.7 pg/ml, 0.75 pg/ml, 0.8 pg/ml, 0.85 pg/ml, 0.9 pg/ml, 0.95 pg/ml, or 1.0 pg/ml or higher is predictive of increased and/or long-term survival, e.g. in a sample obtained from a patient after a dose (e.g. a first dose) of cells have been administered to the patient by ACT, e.g. within 4 weeks of administration of the cells.

In some embodiments, a log 10 transformed level of EBV DNA of one of about 4.0 pg/ml, 3.5 pg/ml, 3.0 pg/ml, 2.5 pg/ml, 2.0 pg/ml, 1.5 pg/ml or lower is predictive of increased and/or long-term survival, e.g. in a sample obtained from a patient after a dose (e.g. a first dose) of cells have been administered to the patient by ACT, e.g. within 4 weeks of administration of the cells, e.g. in a sample obtained from a patient prior to a therapeutic intervention (e.g. chemotherapy and/or ACT) to treat the disease, or a sample obtained from a patient after completion of a therapeutic intervention (e.g. chemotherapy) to treat the disease, and prior to administration of cells to the patient.

In some embodiments, a log 10 transformed level of CCL20 of one of about 1.0 pg/ml, 0.9 pg/ml, 0.8 pg/ml, 0.7 pg/ml, 0.6 pg/ml, 0.5 pg/ml, 0.4 pg/ml, 0.3 pg/ml, 0.2 pg/ml, 0.1 pg/ml or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a log 10 transformed level of CCL22 of one of about 2.0 pg/ml, 1.9 pg/ml, 1.8 pg/ml, 1.7 pg/ml, 1.6 pg/ml, 1.5 pg/ml, or lower is predictive of increased and/or long-term survival.

In some embodiments, a log 10 transformed level of IL-10 of one of about 0.5 pg/ml, 0.4 pg/ml, 0.3 pg/ml, 0.2 pg/ml, 0.1 pg/ml, or lower is predictive of increased and/or long-term survival.

In some embodiments, a log 10 transformed level of IL-8 of one of about 1.0 pg/ml, 0.9 pg/ml, 0.8 pg/ml, 0.7 pg/ml, 0.6 pg/ml, 0.5 pg/ml, 0.4 pg/ml, 0.3 pg/ml, 0.2 pg/ml, 0.1 pg/ml, or lower is predictive of increased and/or long-term survival.

In some embodiments, a log 10 transformed level of VEGF of one of about 2.0 pg/ml, 1.9 pg/ml, 1.8 pg/ml, 1.7 pg/ml, 1.6 pg/ml, 1.5 pg/ml, 1.4 pg/ml, 1.3 pg/ml, 1.2 pg/ml, 1.1 pg/ml, 1.0 pg/ml or lower is predictive of increased and/or long-term survival.

In some embodiments, a log 10 transformed level of CXCL10 of one of about 2.6 pg/ml, 2.55 pg/ml, 2.5 pg/ml, 2.45 pg/ml, 2.4 pg/ml, 2.35 pg/ml, 2.3 pg/ml, 2.25 pg/ml, 2.2 pg/ml, 2.15 pg/ml, 2.1 pg/ml, 2.05 pg/ml, 2.0 pg/ml or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a ratio of the log 10 transformed level of EBV DNA to the log 10 transformed level of IFNγ of one of less than about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0 is predictive of increased and/or long-term survival, e.g. in a sample obtained from a patient after a dose (e.g. a first dose) of cells have been administered to the patient by ACT, e.g. within 4 weeks of administration of the cells. In some embodiments a ratio of the log 10 transformed level of EBV DNA to the log 10 transformed level of IFNγ of less than about 3.0 is predictive of increased and/or long-term survival.

In some embodiments, a ratio of the log 10 transformed level of CCL20 to the log 10 transformed level of IFNγ of one of less than about 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 is predictive of increased and/or long-term survival, e.g. in a sample obtained from a patient after a dose (e.g. a first dose) of cells have been administered to the patient by ACT, e.g. within 4 weeks of administration of the cells.

In some embodiments, a ratio of the log 10 transformed level of CXCL10 to the log 10 transformed level of IFNγ of one of less than about 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1 or 1.0 is predictive of increased and/or long-term survival, e.g. in a sample obtained from a patient after a dose (e.g. a first dose) of cells have been administered to the patient by ACT, e.g. within 4 weeks of administration of the cells. In some embodiments a ratio of the log 10 transformed level of CXCL10 to the log 10 transformed level of IFNγ of less than about 2.5 is predictive of increased and/or long-term survival.

In some embodiments, a ratio of the log 10 transformed level of EBV DNA to the log 10 transformed level of IFNγ of one of less than about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0 and a ratio of the log 10 transformed level of CCL20 to the log 10 transformed level of IFNγ of one of less than about 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, or 0.1 is predictive of increased and/or long-term survival, e.g. in a sample obtained from a patient after a dose (e.g. a first dose) of cells have been administered to the patient by ACT, e.g. within 4 weeks of administration of the cells.

In some embodiments, a ratio of the log 10 transformed level of EBV DNA to the log 10 transformed level of IFNγ of one of less than about 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, or 2.0 and a ratio of the log 10 transformed level of CXCL10 to the log 10 transformed level of IFNγ of one of less than about 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1 or 1.0 is predictive of increased and/or long-term survival, e.g. in a sample obtained from a patient after a dose (e.g. a first dose) of cells have been administered to the patient by ACT, e.g. within 4 weeks of administration of the cells. In some embodiments a ratio of the log 10 transformed level of EBV DNA to the log 10 transformed level of IFNγ of less than about 3.0 and a ratio of the log 10 transformed level of CXCL10 to the log 10 transformed level of IFNγ of less than about 2.5 is predictive of increased and/or long-term survival.

In some embodiments, a normalised count of the number of copies of CD68 RNA (e.g. as determined by nanostring analysis) of about 200, 195, 190, 185, 180, 175, 170, 165, 160, 155, 150, 145, 140, 135, 130, 125, 120, 115, 110, 105, 100, 95, 90 or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a normalised count of the number of copies of S100A8 RNA (e.g. as determined by nanostring analysis) of about 3500, 3250, 3000, 2750, 2500, 2250, 2000, 1750, 1500, 1250, 1000 or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a normalised count of the number of copies of S100A9 RNA (e.g. as determined by nanostring analysis) of about 4500, 4250, 4000, 3750, 3500, 3250, 3000, 2750, 2500, 2250, 2000, 1750, 1500, 1250, 1000 or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a normalised count of the number of copies of LILRSA RNA (e.g. as determined by nanostring analysis) of about 90, 85, 80, 75, 70, 65, 60, 55, 50, 45, 40, 35, 30 or lower is predictive of increased and/or long-term survival, e.g. in a sample obtained from a patient after a dose (e.g. a first dose) of cells have been administered to the patient by ACT, e.g. within 4 weeks of administration of the cells.

In some embodiments, a percentage of monocytes as a proportion of leukocytes of one of fewer than 15%, 14%, 13%, or 12% is predictive of increased and/or long-term survival, e.g. in a sample from a patient prior to a therapeutic intervention (e.g. chemotherapy and/or ACT) to treat the disease, or a sample obtained from a patient after completion of a therapeutic intervention (e.g. chemotherapy) to treat the disease, and prior to administration of cells to the patient.

In some embodiments, a percentage of monocytes as a proportion of live cells is of one of fewer than 70%, 65%, 60%, 55%, 50%, or 45% is predictive of increased and/or long-term survival, e.g. in a sample obtained from a patient prior to a therapeutic intervention (e.g. chemotherapy and/or ACT) to treat the disease, or a sample obtained from a patient after completion of a therapeutic intervention (e.g. chemotherapy) to treat the disease, and prior to administration of cells to the patient.

In some embodiments, a percentage of monocytes as a proportion of live cells is of one of fewer than 60%, 55%, 50%, 45%, 40%, or 35% is predictive of increased and/or long-term survival, e.g. in a sample obtained from a patient after a dose (e.g. a first dose) of cells have been administered to the patient by ACT, e.g. within 4 weeks of administration of the cells.

In some embodiments, a percentage of neutrophils as a proportion of leukocytes of one of fewer than 80%, 75%, 70%, or 65% is predictive of increased and/or long-term survival, e.g. in a sample obtained from a patient after a dose (e.g. a first dose) of cells have been administered to the patient by ACT, e.g. within 4 weeks of administration of the cells.

In some embodiments, a number of lymphocytes as a proportion of the number of leukocytes of one of greater than 15%, 16%, 17%, 18%, 19%, or 20% is predictive of increased and/or long-term survival, e.g. in a sample obtained from a patient after completion of a therapeutic intervention (e.g. chemotherapy) to treat the disease, and prior to administration of cells to the patient, or a sample obtained from a patient after a dose (e.g. a first dose) of cells have been administered to the patient by ACT, e.g. within 4 weeks of administration of the cells.

In some embodiments, a percentage of MDSCs as a proportion of live cells is of one of fewer than 15%, 14%, 13%, 12%, 11%, 10%, 9%, 8%, 7%, 6% or 5% is predictive of increased and/or long-term survival, e.g. in a sample obtained from a patient after completion of a therapeutic intervention (e.g. chemotherapy) to treat the disease, and prior to administration of cells to the patient.

In some embodiments, a percentage of FoxP3+, CTLA4+ Tregs as a proportion of CD3+ cells is of one of fewer than 6%, 5.5%, 5%, 4.5%, 4%, 3.5%, or 3% is predictive of increased and/or long-term survival, e.g. in a sample obtained from a patient prior to a therapeutic intervention (e.g. chemotherapy and/or ACT) to treat the disease.

Predicting Whether the Patient Will be a Long-Term Survivor on Treatment by ACT

The methods of the present invention involve predicting, based on the analysis of a blood-derived sample obtained from the patient, whether the patient will be a long-term survivor on treatment of the disease by ACT.

In some embodiments, the patient is predicted to be a long-term survivor on treatment of the disease by ACT based on determination of one or more positive predictors of increased and/or long-term survival as described herein. In some embodiments, the patient is predicted to be a long-term survivor on treatment of the disease by ACT based on determination of 1, 2, 3, 4, 5, 6, 7, 8, 9, 10 or more positive predictors of increased and/or long-term survival. In some embodiments, the patient is predicted to be a long-term survivor on treatment of the disease by ACT based on determination of at least 1, 2, 3, 4, 5, 6, 7, 8, 9, or 10 positive predictors of increased and/or long-term survival.

Treatment of a Disease by ACT

The present invention provides methods of treating a patient by ACT, a form of immunotherapy. ACT may involve isolating at least one cell from a subject; treating the at least one cell, and; administering the treated cell to a subject. In some embodiments, the subject from which the cell is isolated is the subject administered with the treated cell (i.e., adoptive transfer is of autologous cells). In some embodiments, the subject from which the cell is isolated is a different subject to the subject to which the treated cell is administered (i.e., adoptive transfer is of allogenic T cells).

In some embodiments, the treatment is to expand the number of cells. In some embodiments, the treatment is to generate or expand the number of a cell type which is effective to treat the disease. For example, where the disease is a disease caused or exacerbated by infection with EBV, the treatment of the cells may be to generate or expand the number of EBV-specific cells (e.g. EBV-specific T cells, e.g. EBV-specific CTLs), which are then introduced into the patient. The treatment may be performed in vitro. The treatment may comprise stimulation with EBV-infected cells, e.g. EBV-transformed lymphoblastoid cell line (LCL) cells.

Where the disease is a disease caused or exacerbated by infection with HPV, the treatment of the cells may be to generate or expand the number of HPV-specific cells (e.g. HPV-specific T cells, e.g. HPV-specific CTLs), which are then introduced into the patient. The treatment may be performed in vitro. The treatment may comprise stimulation with HPV-infected cells.

Methods for expanding virus-specific T cells are well known to the skilled person. Typical culture conditions (i.e. cell culture media, additives, temperature, gaseous atmosphere), ratios of responder cells to stimulator cells, culture periods for stimulation steps, etc. can be readily determined by reference e.g. to Bollard et al., J Exp Med (2004), 200(12): 1623-1633 and Straathof et al., Blood (2005), 105(5): 1898-1904, both hereby incorporated by reference in entirety.

In some embodiments the method may comprise one or more of the following steps: taking a blood sample from a subject; isolating and/or expanding at least one T cell from the blood sample; culturing the at least one T cell in in vitro or ex vivo cell culture; stimulating the at least one T cell; collecting the at least one T cell; mixing the modified T cell with an adjuvant, diluent, or carrier; administering the at least one T cell to a subject.

The subject to be treated according to the invention may be any animal or human. The subject is preferably mammalian, more preferably human. The subject may be a non-human mammal, but is more preferably human. The subject may be male or female. The subject may be a patient. A subject may have been diagnosed with a disease or condition requiring treatment, may be suspected of having such a disease or condition, or may be at risk from developing such a disease or condition.

Administration of cells according to the invention is preferably in a "therapeutically effective" or "prophylactically effective" amount, this being sufficient to show benefit to the subject. The actual amount administered, and rate and time-course of administration, will depend on the nature and severity of the disease or disorder. Prescription of treatment, e.g. decisions on dosage etc., is within the responsibility of general practitioners and other medical doctors, and typically takes account of the disease/disorder to be treated, the condition of the individual subject, the site of delivery, the method of administration and other factors known to practitioners. Adoptive transfer of virus specific T cells is described, for example, in Cobbold et al., (2005) J. Exp. Med. 202: 379-386 and Rooney et al., (1998), Blood 92:1549-1555, incorporated by reference hereinabove.

In some embodiments, the method comprises additional therapeutic or prophylactic intervention. In some embodiments, the therapeutic or prophylactic intervention is selected from chemotherapy, immunotherapy, radiotherapy, surgery, vaccination and/or hormone therapy. In some embodiments, the additional therapeutic or prophylactic intervention is performed contemporaneously with treatment of the disease by ACT, and/or may be performed before and/or after treatment of the disease by ACT.

In one aspect, the present invention provides a method of treating a patient by adoptive cell transfer (ACT), the method comprising:
(i) administering a dose of cells to a patient;
(ii) analysing a blood-derived sample obtained from the patient for one or more prognostic markers of long-term survival on treatment of a disease by ACT;
(iii) based on the analysis of step (ii), predicting long-term survival of the patient by treatment of the disease by ACT; and
(iv) administering one or more further doses of cells to the patient.

In some embodiments, the analysis/prediction of whether the patient will be a long-term survivor on treatment of the disease by ACT influences the decision as to whether to treat, or continue to treat, the disease by ACT.

In some embodiments, the method is used to stratify patients for which treatment by ACT is predicted to be associated with long-term survival, as compared to patients for which treatment by ACT is not predicted to be associated with long-term survival.

That is, the present invention may be employed to the identification and/or selection of (i) a sub-population of patients suffering from a disease to be treated by ACT in which treatment by ACT is predicted to be associated with long-term survival, and/or (ii) a sub-population of patients suffering from a disease to be treated by ACT in which treatment by ACT is predicted not to be associated with long-term survival.

Accordingly, in a related aspect the present invention provides a method of selecting a patient for treatment of a disease by adoptive cell transfer (ACT), comprising:
(i) analysing a blood-derived sample obtained from the patient for one or more prognostic markers of long-term survival on treatment of a disease by ACT;
(ii) based on the analysis of step (i), predicting whether the patient will be a long-term survivor on treatment of the disease by ACT; and
(iii) selecting a patient predicted to be a long-term survivor on treatment of the disease by ACT for treatment of the disease by ACT.

In some embodiments, the method additionally comprises an initial step of administering a dose of cells to a patient. The dose of cells may be administered in accordance with a method of treatment of the disease by ACT, or may be administered as an initial screening step to evaluate the likely response of the patient to treatment of the disease by ACT.

In a further related aspect the present invention provides a method of selecting a patient for continued treatment of a disease by adoptive cell transfer (ACT), comprising:
(i) administering a dose of cells to a patient in accordance with treatment of a disease by ACT;
(ii) analysing a blood-derived sample obtained from the patient for one or more prognostic markers of long-term survival on treatment of a disease by ACT;
(iii) based on the analysis of step (ii), predicting whether the patient will be a long-term survivor on treatment of the disease by ACT; and
(iv) selecting a patient predicted to be a long-term survivor on treatment of the disease by ACT for continued treatment of the disease by ACT.

The method may further comprise step (v) administering one or more doses of cells to patients selected in (iv).

Improving Long-Term Survival of a Patient on Treatment of the Disease by ACT

The present invention also provides methods of treatment of a disease by ACT, and/or methods for enhancing the effectiveness of treatment of a disease by ACT, comprising administering to a patient one or more agents for modifying the level of one or more prognostic markers of long-term survival on treatment of a disease by ACT.

In some embodiments, the methods comprise administering one or more agents for decreasing MDSC number or activity and/or decreasing regulatory T lymphocyte number or activity, for increasing effector T lymphocyte number or activity, and/or for reducing the amount of an infectious agent associated with the disease.

In some embodiments, the one or more agents are administered to a patient after analysis in accordance with a method for predicting whether a patient will be a long-term survivor on treatment of a disease by ACT, a method of treating a patient by ACT, or a method of selecting a patient for treatment of a disease by ACT as described herein. In some embodiments, the one or more agents are administered based on prediction that the patient will not be a long-term survivor on treatment of the disease by ACT.

In some embodiments, the one or more agents are administered prior to administration of a dose of cells to the patient. In some embodiments the one or more agents are administered after a dose of cells has been administered to the patient. In some embodiments, the one or more agents are administered contemporaneously with treatment of the disease by ACT.

Also provided by the present invention is an agent for use in a method described herein, use of an agent in the manufacture of a medicament for use in a method described herein, and the use of an agent in a method described herein.

The skilled person is well able to identify agents for decreasing MDSC number or activity and/or decreasing regulatory T lymphocyte number or activity, for increasing effector T lymphocyte number or activity, and/or for reducing the amount of an infectious agent associated with the disease.

In some embodiments, the agent capable effect reduced or increased gene/protein expression and/or function by influencing transcription, mRNA processing (e.g. splicing), mRNA stability, translation, post-translational processing, protein stability, protein degradation and/or protein function/activity. Examples of agents include antagonist/agonist antigen-binding molecules, nucleic acids (e.g. siRNA, shRNA), small molecule inhibitors/agonists etc.

Kits

The present invention also provides kits for use in accordance with the methods described herein.

In some embodiments the kit may be suitable for analysing a blood-derived sample as described herein for one or more prognostic markers of long-term survival on treatment of a disease by ACT. The kit may be employed to predict whether or not a patient will be a long-term survivor on treatment of the disease by ACT.

According the present invention provides a kit comprising means for detecting a marker of MDSC number or activity and/or regulatory T lymphocyte number or activity, and means for detecting a marker of effector T lymphocyte number or activity, optionally further comprising means for detecting a marker of the amount of an infectious agent associated with the disease.

The kit may have at least one container having a predetermined quantity of: one or more reagents for detecting the level of one or more markers of MDSC number or activity and/or one or more markers of regulatory T lymphocyte number or activity, one or more reagents for detecting the level of one or more markers of effector T lymphocyte number or activity, and/or one or more reagents for detecting the level of one or more markers of the amount of an infectious agent associated with the disease.

The skilled person is readily able to identify reagents suitable for determining the level of the relevant gene/protein expression or activity in a sample. Suitable reagents may include e.g. oligonucleotide primers, ELISA antibody pairs, aptamers etc. Suitable reagents may include detectable labels for detection and quantification In some embodiments, the kit contains all of the components necessary and/or sufficient to perform an assay on a blood-derived sample for predicting whether a patient will be a long-term survivor on treatment of the disease by ACT, including all controls, instructions/directions for performing assays, and any necessary software for analysis and presentation of results.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

EXAMPLES

In the following Examples, the inventors describe analysis of samples collected from a Phase II clinical trial in which Epstein-Barr virus (EBV)-positive nasopharyngeal carcinoma (NPC) patients were treated with gemcitabine and carboplatin for four cycles, followed by treatment by adoptive transfer of autologous, in vitro expanded, EBV-specific CD8$^+$ T-cells.

The inventors undertook a multifactorial analysis to determine systemic immune sera correlates that influence and determine successful therapy, and examined the cellular immune environment using cryopreserved PBMCs from samples collected before and after chemotherapy, and throughout immunotherapy, to evaluate the immunosuppressive state of the patients.

The inventors demonstrate key differences between non-survivors and long-term survivors in terms of Teffector:Treg ratios and whether or not there is expansion or contraction of the myeloid-derived suppressor cell (MDSC) compartment.

Example 1: Experimental Procedures 1.1 Immunotherapy Trial and Sample Collection A Phase H clinical trial was performed in which Epstein-Barr virus (EBV)-positive nasopharyngeal carcinoma (NPC) patients were treated with gemcitabine and carboplatin for four cycles, followed by treatment by adoptive transfer of autologous, in vitro expanded, EBV-specific CD8$^+$ T-cells.

The results demonstrated unprecedented efficacy. The two-year overall survival rate was 62.9%, and the three-year overall survival rate was 37.1%. These two- and three-year overall survival rates are amongst the best survival rates for treatment of advanced NPC.

Analysis of the Phase II trial data showed that there was a positive correlation between long-term survivors and the ability of their CTLs to produce IFN-γ in response to LMP2 antigen presentation.

Throughout the immunotherapy trial peripheral blood was sampled from the patients. The time points examined were:
Pre chemotherapy (T-1);
Post chemotherapy, pre-immunotherapy (T0);
Post first CTL infusion (T1);
Post second CTL infusion (T2); and
Post third CTL infusion (T3).

1.2 Serum Cytokine Analysis

A 27-plex human cytokine and chemokine luminex multiplex bead array assay kit (Invitrogen; Carlsbad, Calif.) was used to measure levels of the following cytokines in diluted plasma obtained from samples: IL-3, IL-4, IL-6, IL-8, IL-9, IL-10, IL-15, IL-17, IL-21, (CXCL10) IP-10, CCL3 (MIP-1α), CCL4 (MIP-1β), CCL20 (MIP-3sα), MCP-1, IFN-α2, IFN-γ, EGF, FGF-2, VEGF, TGFA, CD40L, fractalkine, GM-CSF, G-CSF, GRO, MDC, and eotaxin.

Plates were washed using Biotek ELx405 washer (Biotek, USA) and 'read' with Flexmap 3D systems (Luminex Corp, Austin, Tex., USA) as per the manufacturer's instructions. Data were analyzed using Bio-Plex manager 6.0 software with a 5-parameter curve-fitting algorithm applied for standard curve calculations.

1.3 Immunophenotyping of PBMCs

PBMCs obtained from frozen patient samples collected at the timepoints T-1 to T3 were stained with two different fluorescently labeled monoclonal antibody panels (Treg panel or MDSC panel) to determine cell lineage and activation status.

Treg panel: BUV 395 ant-CD25, Pacific Blue anti-FoxP3, BV 711 ant-CD127, FITC anti-CD4, PE anti-CTLA4, PECF594 anti-CD45RA, PECy5 anti-CD3, PE Cy7 anti-CCR7, near infrared live/dead cell stain.

Tregs were identified using a single cell gate, live/dead cell negative, CD3 positive, CD4 positive, CD25 positive, CD127 negative, FOXP3 positive, CTLA4 positive gating strategy.

MDSC panel: BUV 395 anti-CD15, FITC anti-CD16, PE anti-CD33, PECF594 anti-CD34, PE Cy7 anti-CD11b, APC anti-CD14, APC H7 anti-HLA-DR, violet live/dead cell stain.

Monocytic MDSCs were identified using a single cell gate, live/dead cell negative, CD16 negative, CD15 negative, CD34 negative, CD11b positive, CD33 positive, CD14 intermediate, HLA-DR negative-low gating strategy. Cells were acquired using an LSRII (BD Biosciences) flow cytometer. Data was analysed using Diva (BD Biosciences) and Flowjo (Treestar) software.

1.4 RNA Isolation $1 \times 10^5$ thawed PBMCs from time points T-1, T0, T1, T2 and T3, were pelleted by centrifugation in eppendorf tubes. Samples subsequently underwent RNA extraction using a QIAGEN RNAEasy Micro kit. Samples were processed according to the manufacturer's guidelines. Final elution volume was in 15 μl RNase free water.

1.5 Nanostring Processing

Gene expression was analysed using a Nanostring Pan-Cancer Immune Panel. 100 ng of each patient sample was prepared as per the manufacture's guidelines. Quantification of gene expression was determined using the nCounter platform, raw counts were processed using nSolver. Counts were normalised using the ComBat method.

1.6 Bayesian Network Analysis

Bayesian networks of combined luminex and nanostring data for each separate time point, were calculated using BayesiaLab. Two-year survival status was excluded from the initial network, which was formed using the maximum spanning tree algorithm (structural coefficient=1). Nodes were then clustered using the variable clustering function. Taboo learning, with two-year survival included, was utilised to form the final network.

1.7 Statistical Analysis

Correlation with overall survival was evaluated by analysis using Spearman's ranked correlation. Correlation with two-year survival was anaylsed using two-way ANOVA with Bonferroni correction.

Example 2: Long-Term Survivors Experience Increased Lymphoid but Decreased Myeloid Numbers Post CTL Immunotherapy Throughout the immunotherapy trial peripheral blood was sampled from the patients. In order to assess the impact of immunotherapy analysis was focused on the time point two weeks after the first immunotherapy infusion (T1; see FIG. 1).

The numbers of peripheral blood leukocytes at time point T1 were assessed to detect any gross changes in the immune system as a result of immunotherapy. The results are shown in FIGS. 2A to 2E.

Figure 2A:
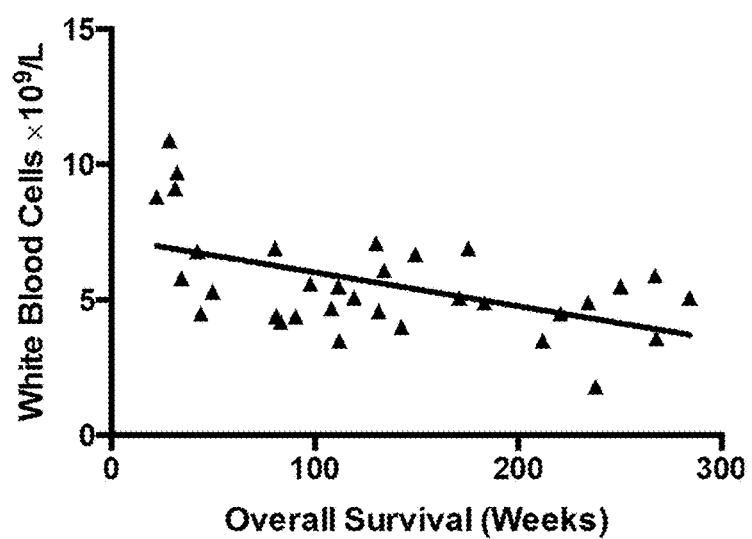
FIGS. 2A-2D. Graphs showing numbers/percentages of peripheral blood leukocytes at two weeks after first CTL infusion (i.e. at time point T1) vs. overall survival.
Figure 2B:
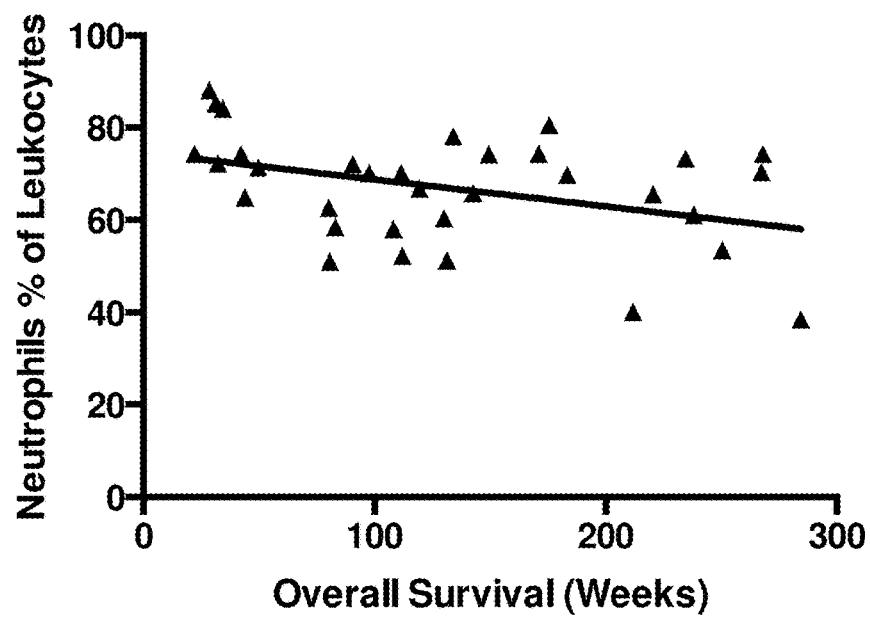
Figure 2C:
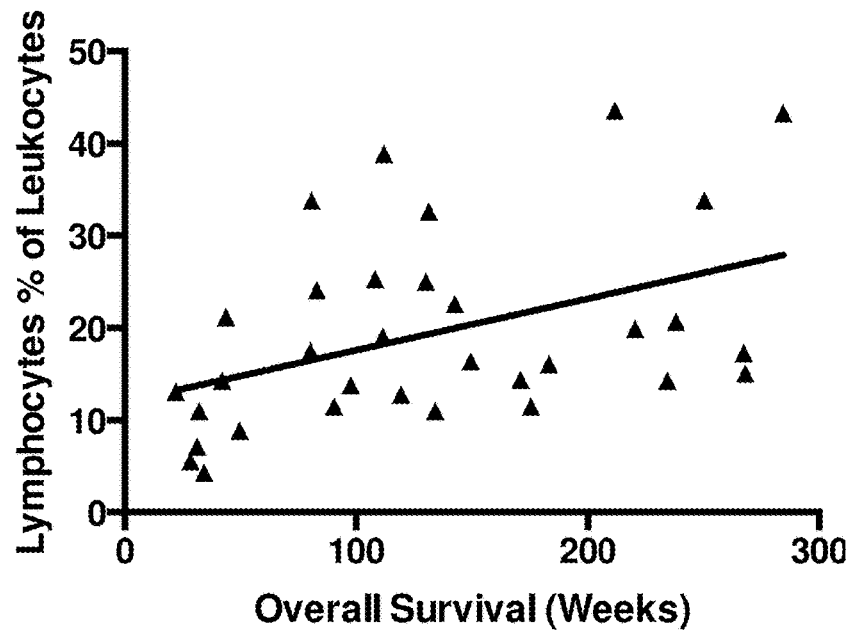
Figure 2D:
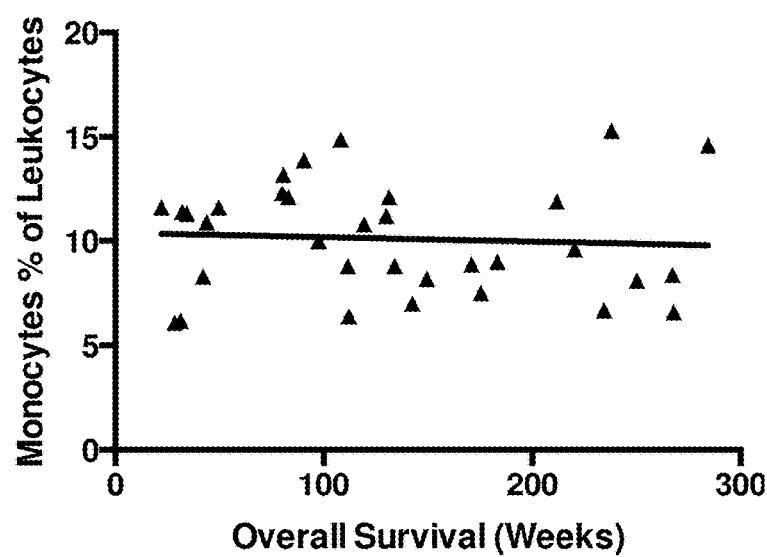

There was a significant negative correlation between the number of leukocytes and overall survival (r=−0.43; FIG. 2A). Neutrophil numbers (as a proportion of leukocytes) were also significantly, negatively associated with survival, albeit with poor correlation (r=−0.32; FIG. 2B). Conversely there was a significant positive correlation between lymphocyte numbers (as a proportion of leukocytes) and overall survival (r=0.46; FIG. 2C). No correlation was observed between monocyte number (as a proportion of leukocytes) and overall survival (FIG. 2D). Analysis of leukocyte numbers at time points before immunotherapy (T0) or before chemotherapy (T-1) did not reveal a statistically significant correlation with overall survival (FIG. 3; Table 1).

Taken together, the results suggested that long-term survivors experience a shift in leukocyte composition within two weeks after the first immunotherapy injection, results in decreased numbers of myeloid cells and increased numbers of effector T lymphocytes. The results also demonstrate that this change in the immune cell population occurs as a direct result of immunotherapy, and is not attributable to chemotherapy.

Example 3: Successful CTL Immunotherapy Results in Increased IFNγ

In order to assess whether or not the increase in lymphocyte numbers was also influencing viral load and cytokine production, patient sera was analysed for cytokine production by luminex assay, and EBV DNA was quantified by qPCR. The results of the analyses are shown in FIG. 4A to 4F. The data shown in FIGS. 4A to 4D, 5, 6 and 7A and 7B is based on analysis of serum obtained from samples isolated at time point T1, i.e. two weeks after the first infusion of EBV-specific CTL.

Figures 3, 4A:
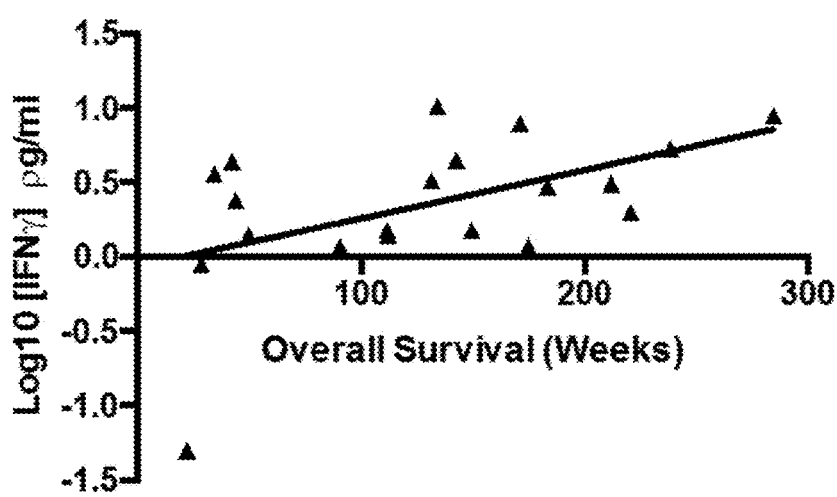
FIG. 3. Table 1 showing the results of statistical analysis of correlation of peripheral blood leukocyte numbers with overall survival at different time points.
FIGS. 4A-4D. Graphs showing serum levels of cytokines/chemokines and EBV DNA at two weeks after first CTL infusion (i.e. at time point T1) vs. overall survival.
Figure 4B:
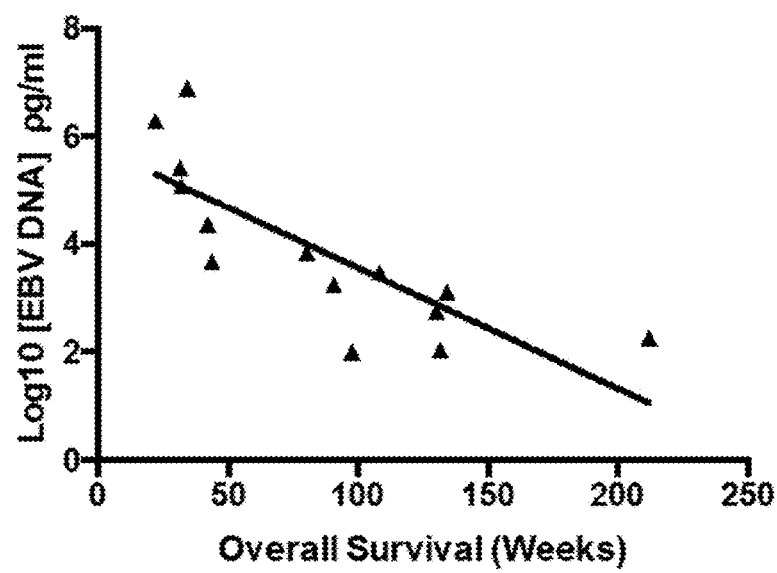
Figure 4C:
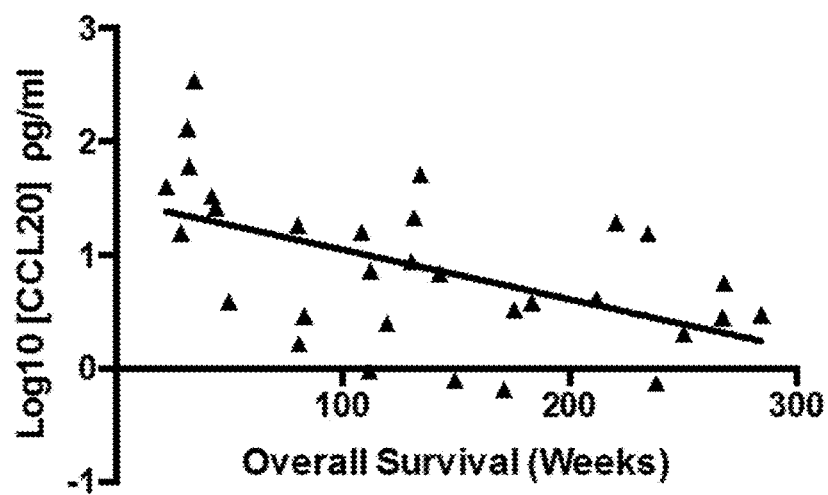
Figures 4D, 5:
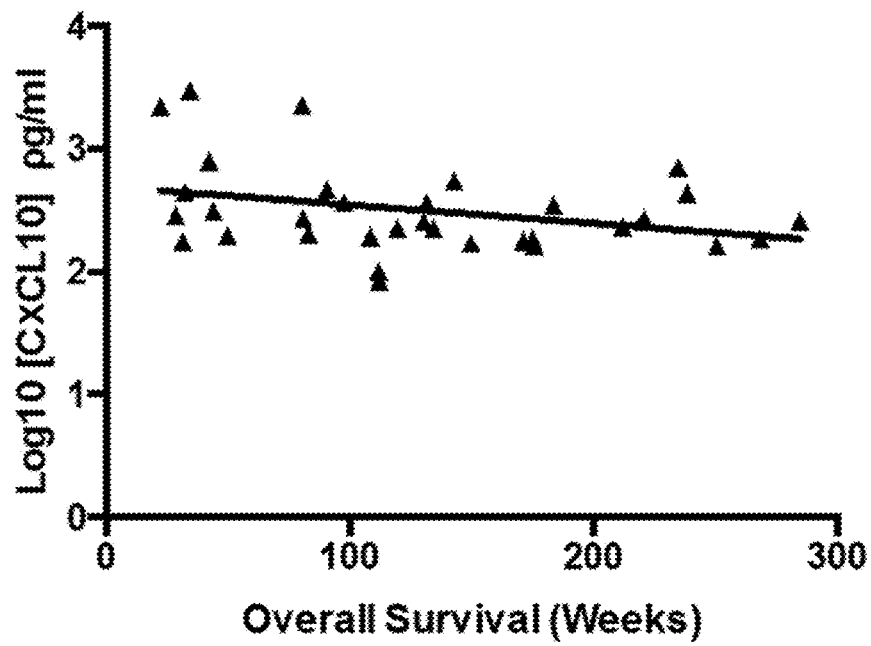
FIG. 5. Table 2 showing the results of statistical analysis of correlation of serum levels of cytokines/chemokines and EBV DNA with overall survival at different time points.

Within two weeks after the first immunotherapy infusion there was a significant positive correlation between IFNγ production and survival (FIG. 4A). Prior to immunotherapy (i.e. at T0), there was no correlation was observed between survival and IFNγ concentrations in the sera (Table 2, FIG. 5). Conversely, survival was strongly correlated with a significant decrease in EBV viral load (FIG. 4B). Production of myeloid-expressed chemokines such as CCL20 was similarly decreased in long-term survivors (FIG. 4C). Whilst other cytokines produced by myeloid cells such as CCL10 were not significantly associated with survival (FIG. 4D).

In order to investigate these correlations to serve as biomarkers for survival associated with treatment with autologous EBV-specific CTL, patients were sorted into groups of patients which survived for two years (Two Year Survivor) and patients which did not survive for two years (Non Survivor). Two-year survival was chosen as a cutoff due to the fact that EBV+ Stage IV NPC patients have a median survival range of 11-22 months.

Figure 6A:
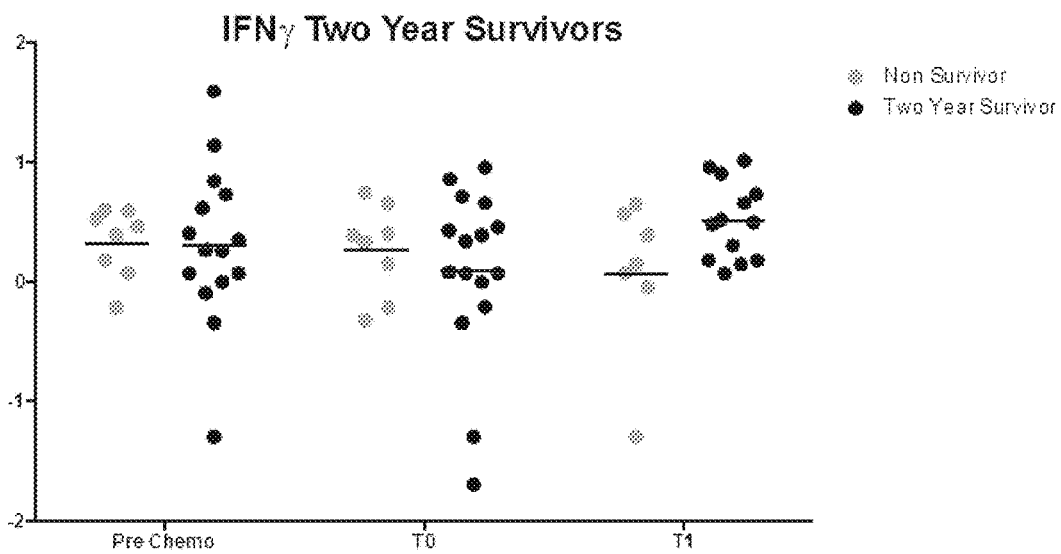
FIGS. 6A-6B. Graphs showing single analyte analysis of serum levels of FIG. 6A IFNγ and FIG. 6B EBV DNA at two weeks after first CTL infusion (i.e. at time point T1).
Figure 6B:
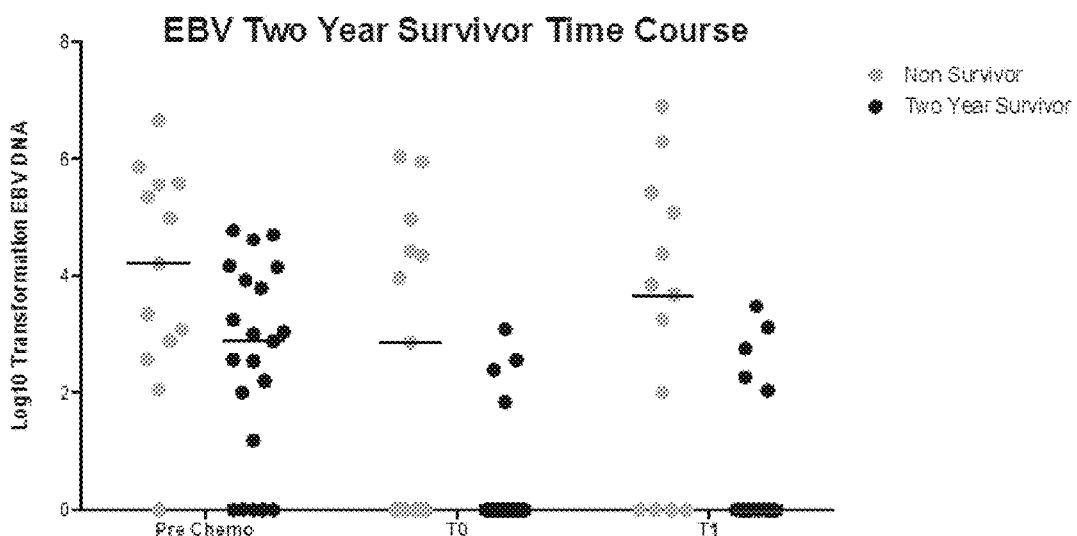

Analysis of single analytes did not sufficiently stratify non-survivors vs. two-year survivors (FIGS. 6A and 6B). The inventors therefore analysed ratios of the serum levels of several different cytokines and EBV DNA to the only cytokine which was positively correlated with survival, IFNγ. IFNγ was used as the consequent, and analytes which correlated with non-survival were used as the antecedent.

Figure 7A:
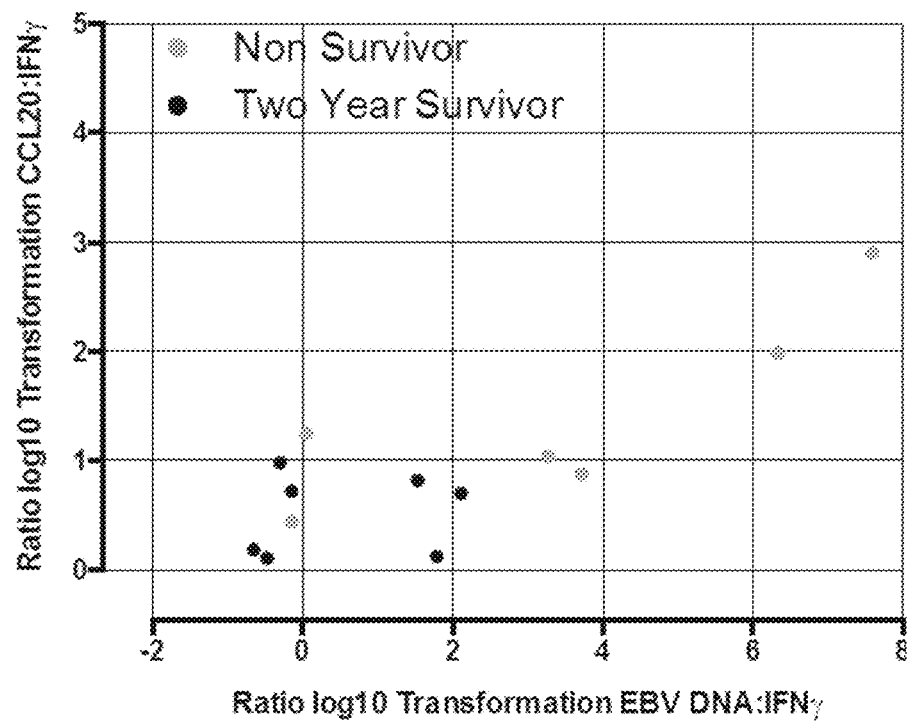
FIGS. 7A-7B. Graphs showing serum analyte ratio analysis at two weeks after first CTL infusion (i.e. at time point T1).
Figure 7B:
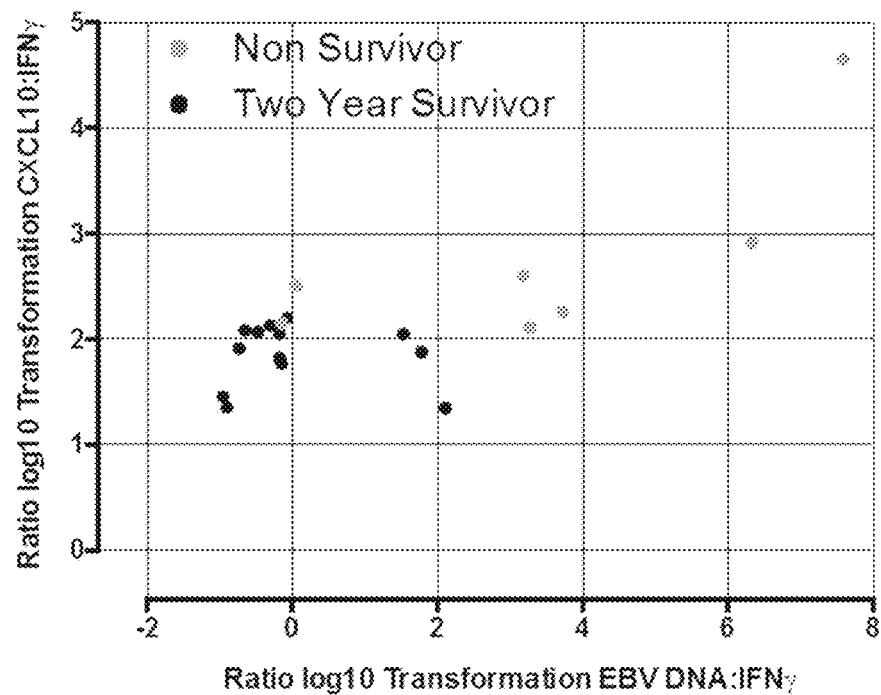

The results are shown in FIGS. 7A and 7B. Using a combination of EBV DNA:IFNγ vs CCL20:IFNγ, or of EBV DNA:IFNγ vs CCL10:IFNγ, the inventors were able to correctly identify two-year survivors with a true positive rate of 85%. Thus the inventors demonstrated the ability of the serum levels of combinations of markers at two weeks after the commencement of treatment with autologous EBV-specific CTL to predict long-term survival of patients.

In order to validate the findings, the ratiometric values were inputted into the Weka machine learning software algorithm. The logistic regression methodology was also able to correctly classify patients with a success rate of 85%. To evaluate the effectiveness of the ratios instead of actual values, the same data was inputted replacing the ratios with single analyte measurements. Removal of one of the analytes from the ratios reduced the correctly classified rate to 57%.

Together, the results show that successful immunotherapy induces greater IFNγ production in long-term survivors, whilst the level of production of chemokines produced by myeloid cells is reduced.

Example 4: Non-Survivors Express Increased Transcripts Associated with Myeloid Cells The inventors next decided to investigate the reasons for therapeutic failure in individuals who survived for less than two-years.

Figure 8:
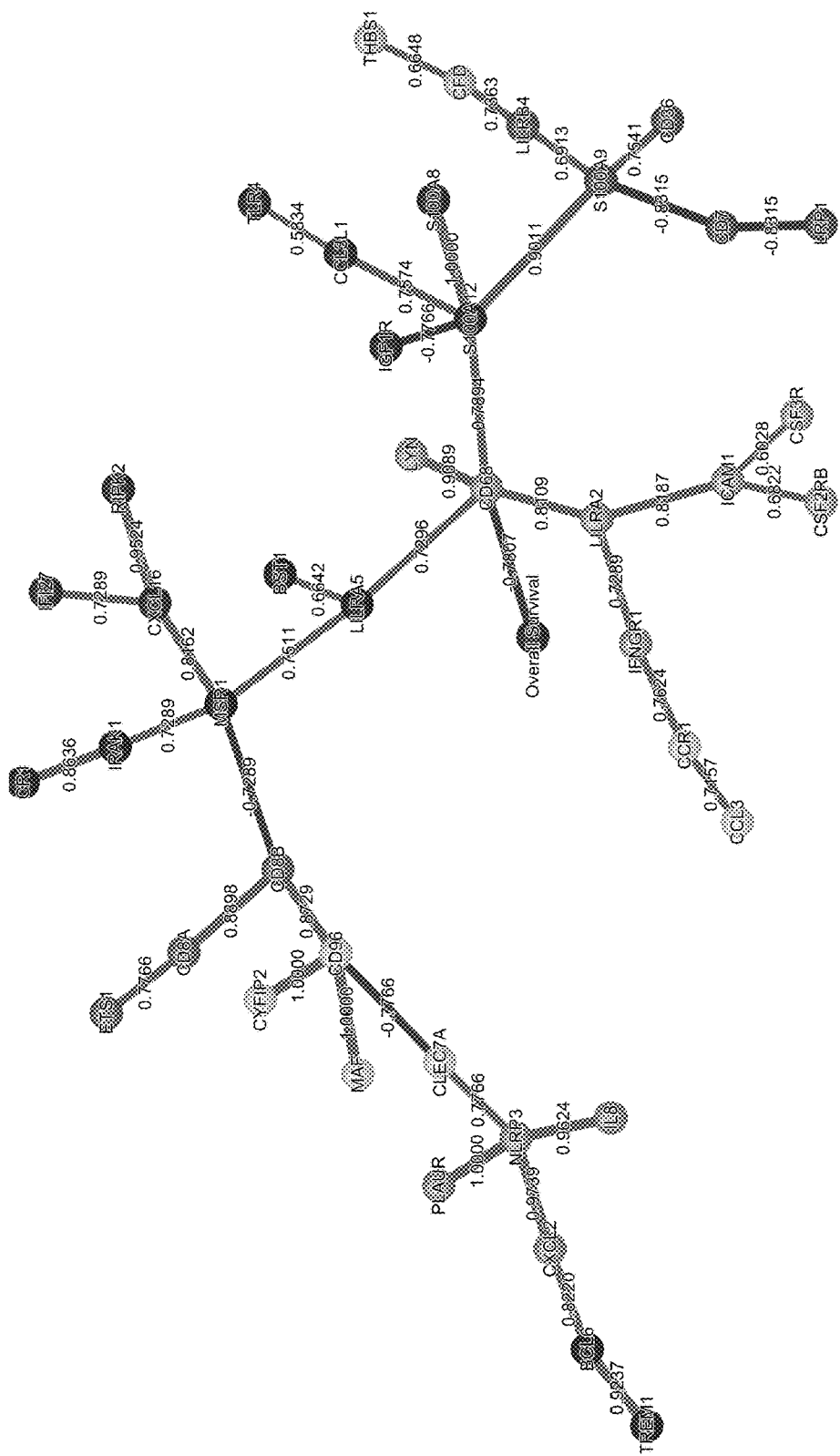
FIG. 8. Schematic showing Bayesian network of nanostring analysis of RNA obtained from patient PBMCs at time point T1.
Figure 10A:
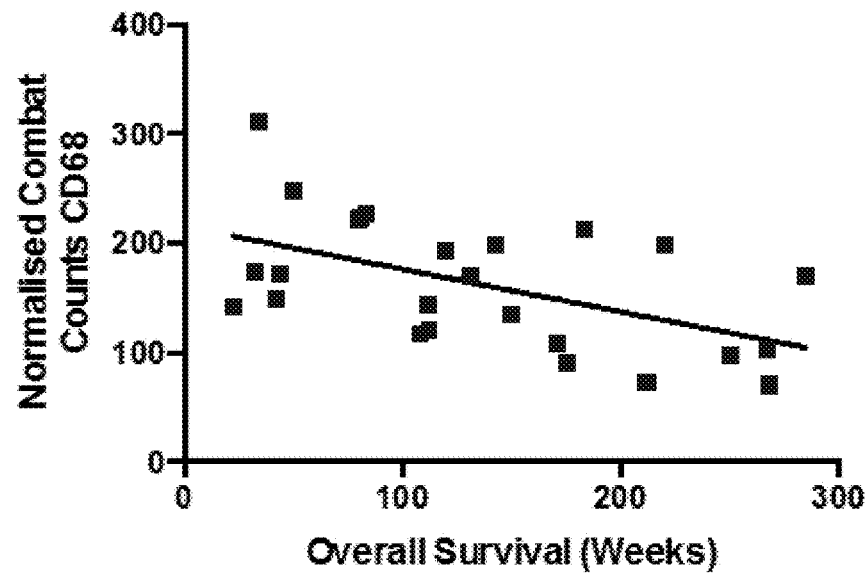
FIGS. 10A-10C. Graphs showing level of RNA transcripts at two weeks after first CTL infusion (i.e. at time point T1) vs. overall survival.
Figure 10B:
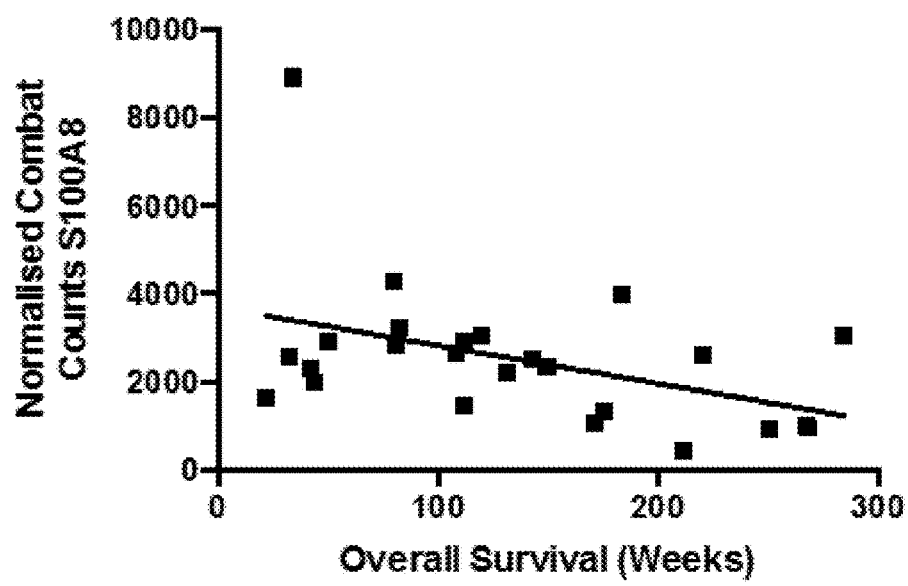
Figure 10C:
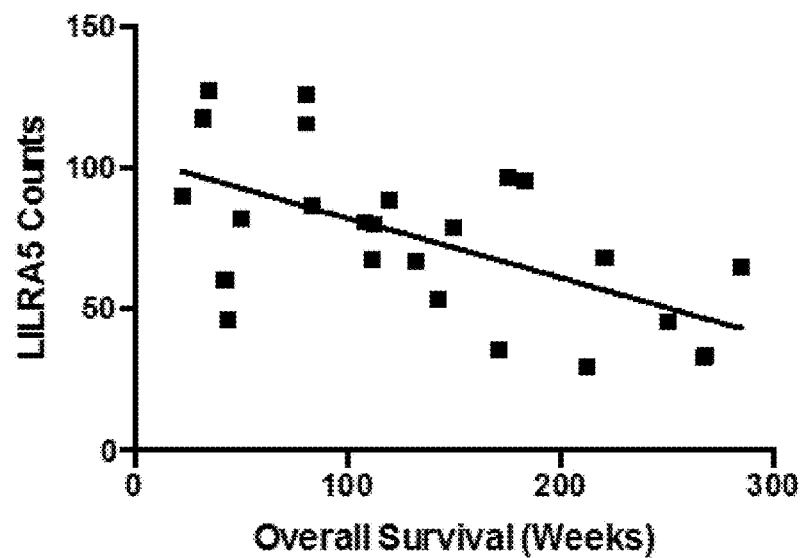

Patient PBMCs obtained at time point T1 were subjected to nanostring analysis for transcript quantification. RNA counts were normalized, filtered for significance and subsequently analysed using a Bayesian network (FIG. 8). Examination of this network revealed an enrichment of transcripts associated with markers of myeloid cells and immune inhibitory markers. Spearman's ranked correlation was used to further filter and identify associations with therapeutic failure. The strongest correlations observed with overall survival were CD68, LILRA5, and S100A8 transcription, all of which are associated with myeloid cells and inhibitory marker expression (FIGS. 10A, 10B, and 10C).

In addition, CD8 transcription was also found to be significantly associated with overall survival (Table 3, FIG. 9).

Figure 18A:
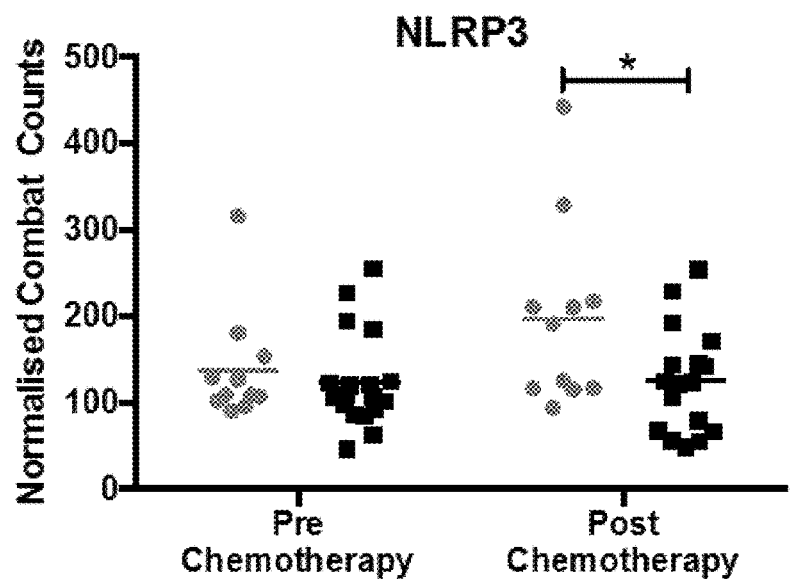
Figure 18B:
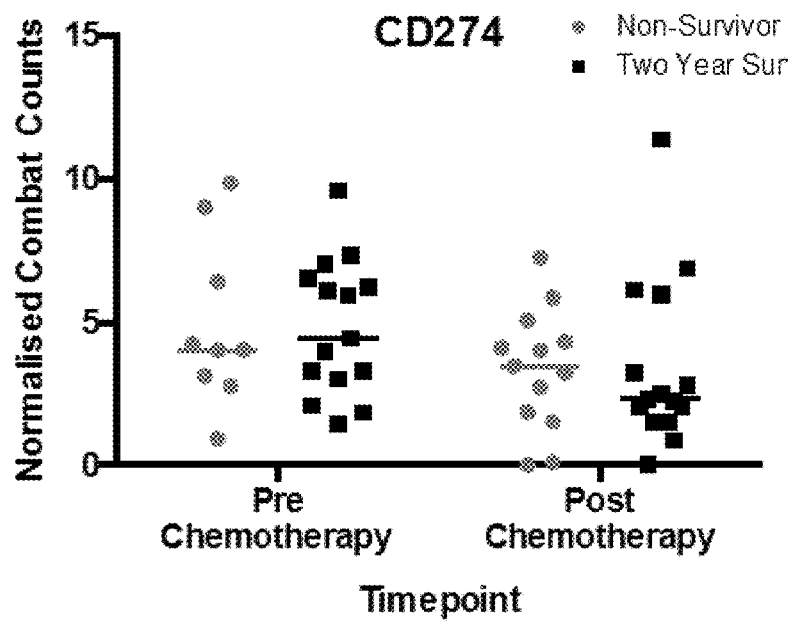
Figure 18C:
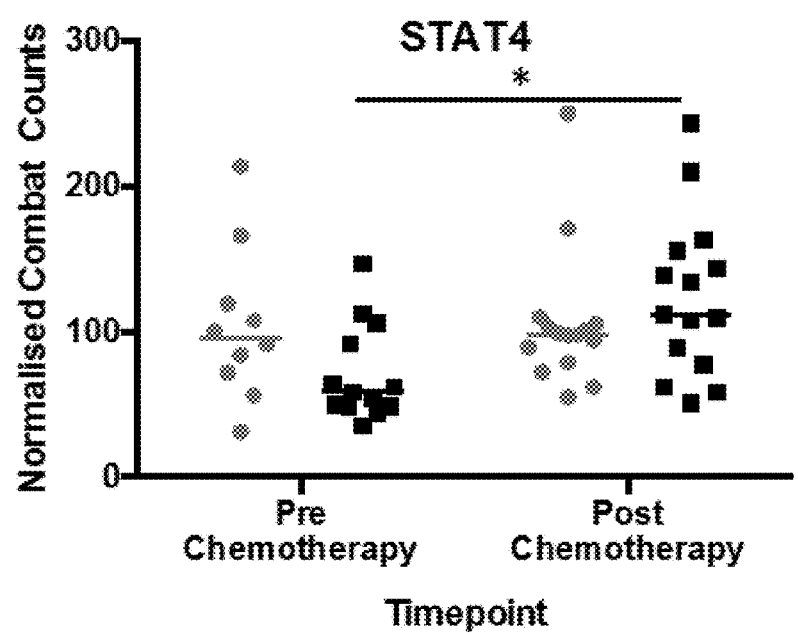

FIG. 18A to 18C shows nanostring analysis of transcription of the inflammasome and inhibitory markers NLRP3, CD274 (PD-L1) and STAT4 at time points T-1 (pre-chemotherapy) and T0 (post-chemotherapy) for non-survivors and long-term survivors.

Figure 19:
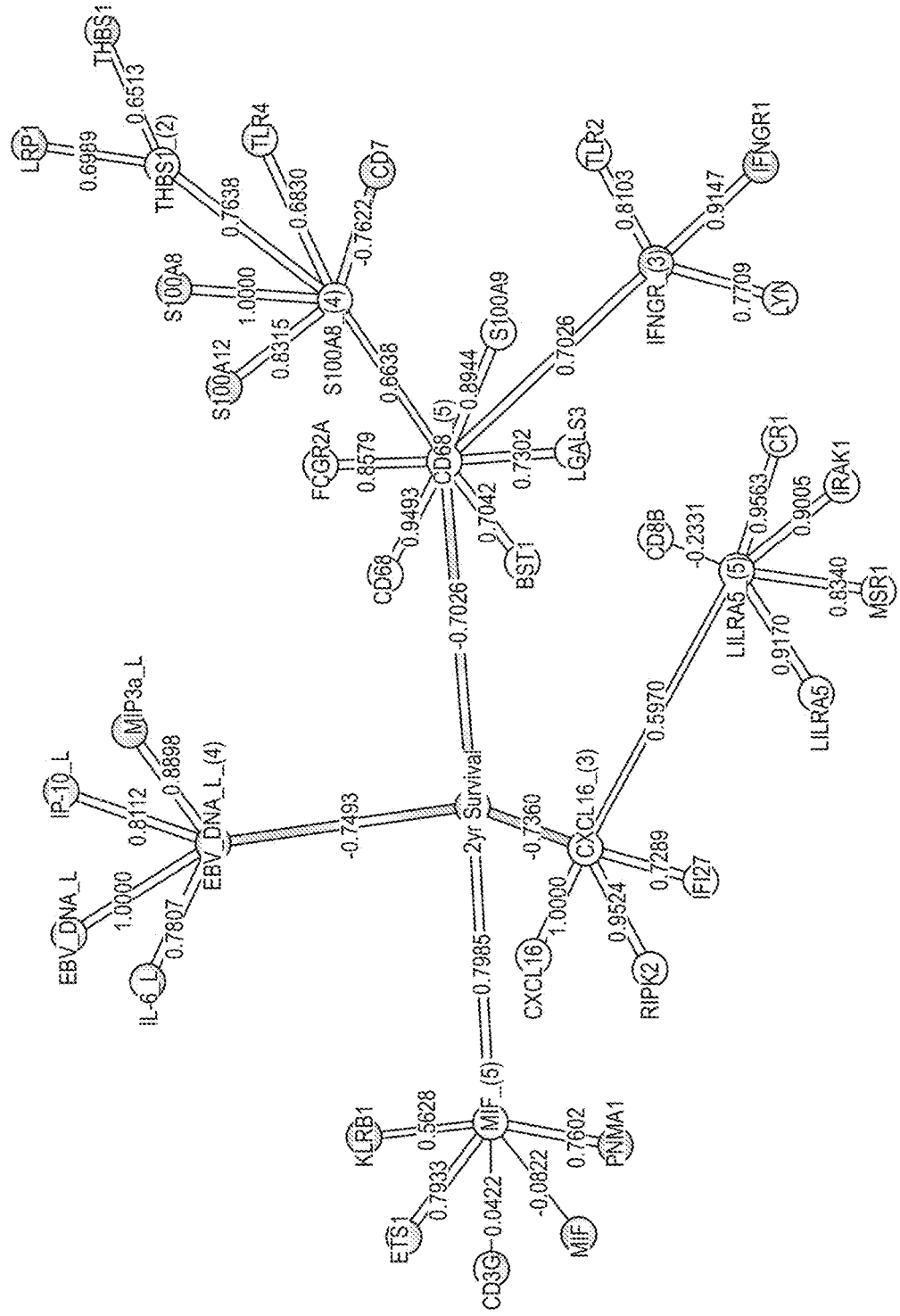
FIG. 19. Schematic showing Bayesian network of nanostring analysis of RNA obtained from patient PBMCs at time point T1.
Figure 20A:
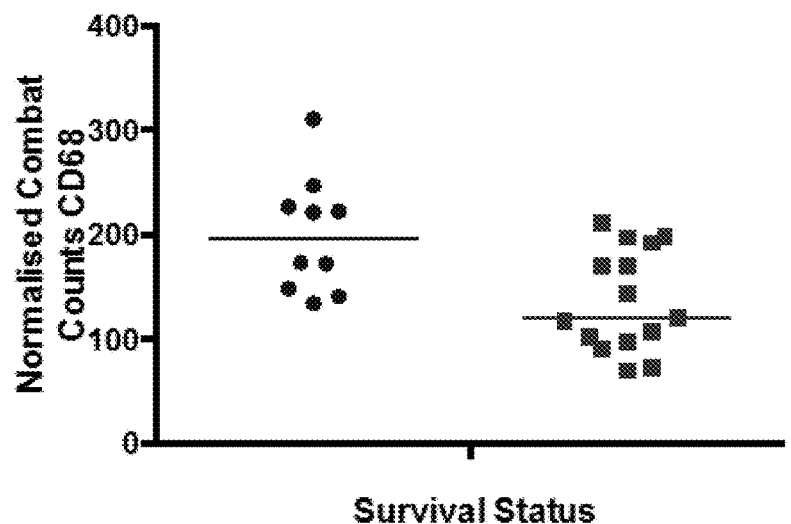
FIGS. 20A-20C. Graphs showing level of RNA transcripts for different markers at T1 in non-survivors (circles) and long-term survivors (more than 2 years; squares).
Figure 20B:
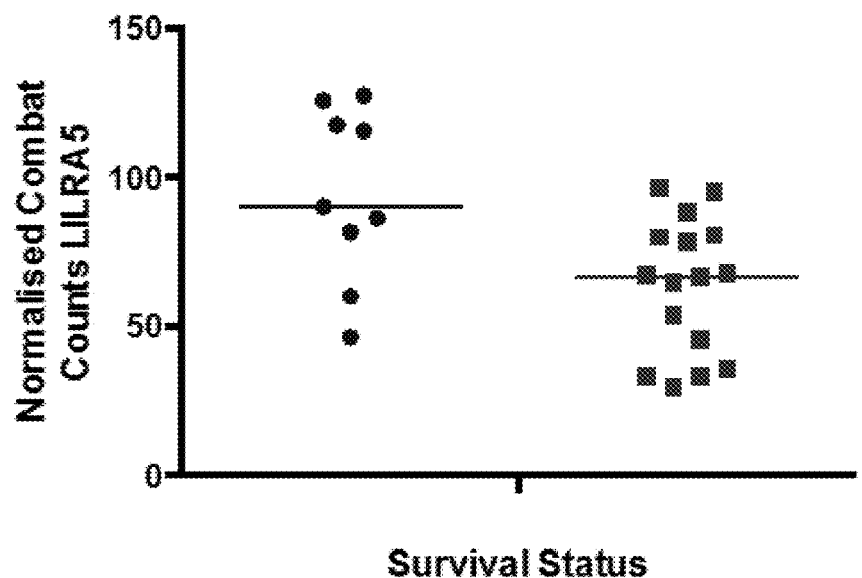
Figure 20C:
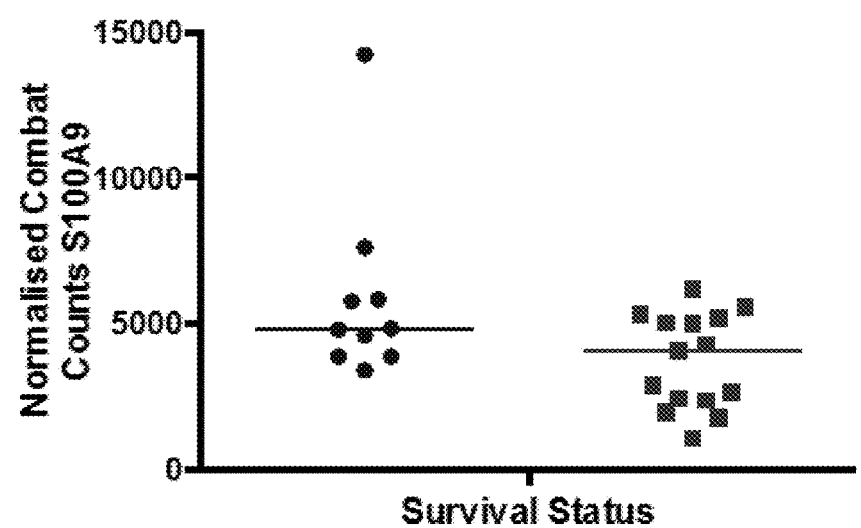

FIGS. 19 to 21 show the results of further nanostring and Bayesian network analysis of RNA obtained from patient PBMCs at time point T1. Examination of this network revealed an enrichment of transcripts associated with myeloid and inhibitory markers. Spearman's ranked correlation was used to further filter and identify associations with therapeutic failure. The strongest correlations observed with overall survival were CD68, LILRA5, and S100A9 transcription, all of which are associated with myeloid cells and inhibitory marker expression (FIGS. 20A, 20B, and 20C). In addition, CD8B transcription was also found to be significantly associated with overall survival (Table 4, FIG. 21).

Together, these results suggest that the presence of a myeloid/inhibitory leukocyte signature in the peripheral blood negatively impacts long-term patient survival, potentially by creating an inhibitory environment which negatively influences CTL infusion efficacy.

Example 5: Non-Survivors Experience an Increase of Myeloid-Derived Suppressor Cells Post Chemotherapy In order to further examine the impact of this myeloid/inhibitory signature on survival the inventors extended analysis of the whole blood counts to time points before immunotherapy (i.e. T-1 and T0), as it has recently been shown that successful T cell vaccination relies on ablation of the myeloid compartment (Welters, M. J., van der Sluis, T. C., van Meir, H., Loof, N. M., van Ham, V. J., van Duikeren, S., et al. (2016). Vaccination during myeloid cell depletion by cancer chemotherapy fosters robust T cell responses. *Science Translational Medicine*, 8(334), 334ra52-334ra52. http://doi.org/10.1126/scitranslmed.aad8307).

Figure 22:
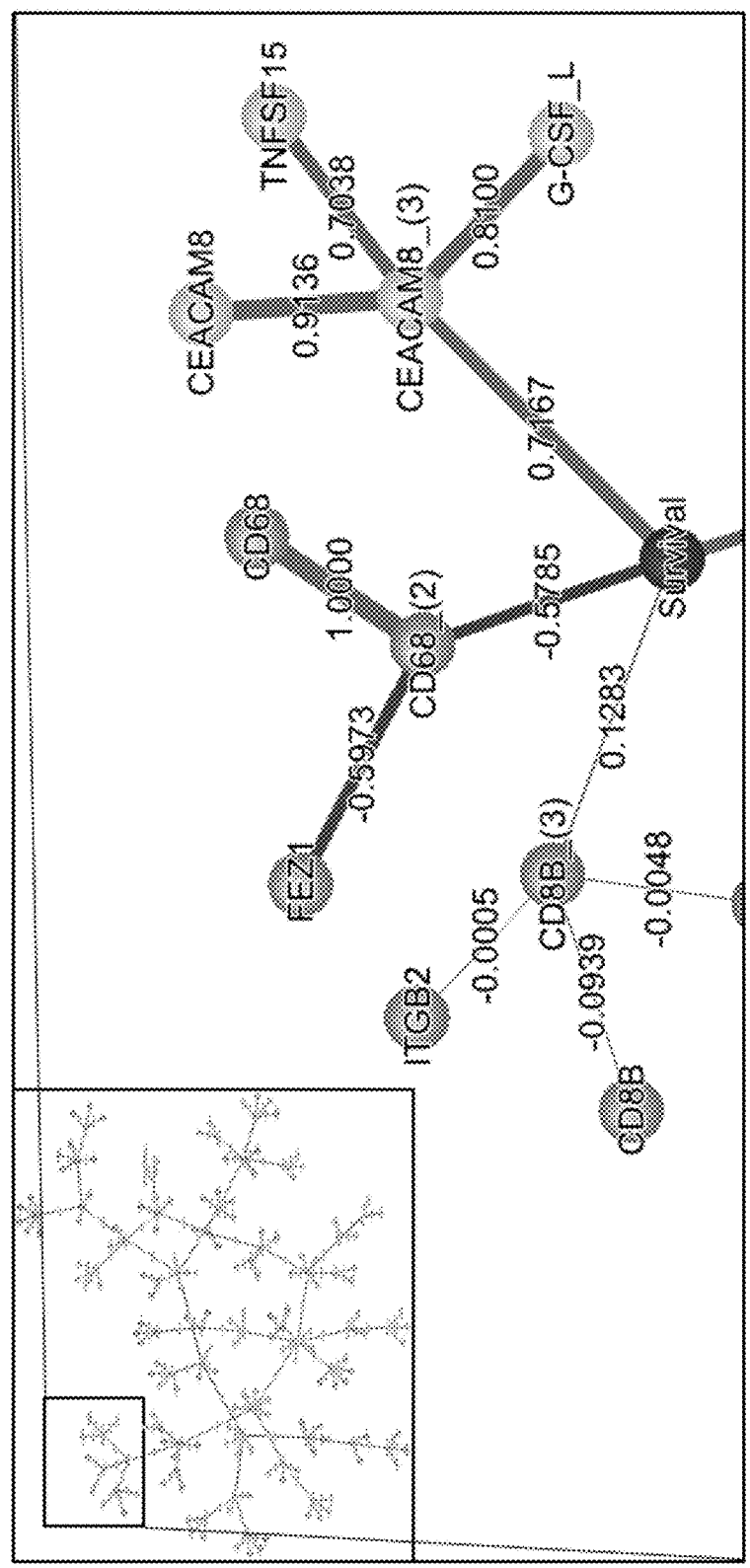
FIG. 22. Schematic of Bayesian network of nanostring analysis of RNA obtained from patient PBMCs at time point T0.

Bayesian network analysis of the post chemotherapy time-point (i.e. T0) revealed that CD68 expression was negatively correlated with two-year survival. This suggests that increased presence of myeloid cells contribute to decreased patient survival after immune cell ablation (FIG. 22; Table 5, FIG. 23).

Figure 11A:
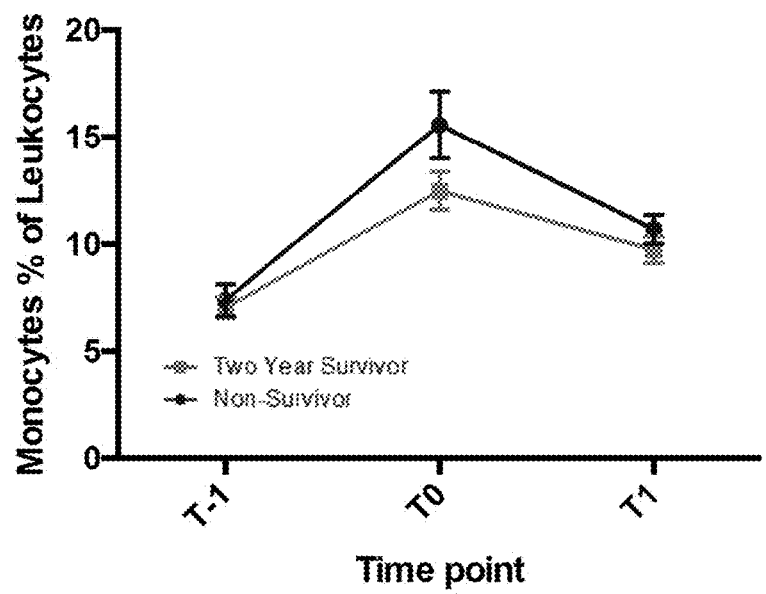
FIGS. 11A-11B. Graphs showing monocyte numbers at different time points.
Figure 11B:
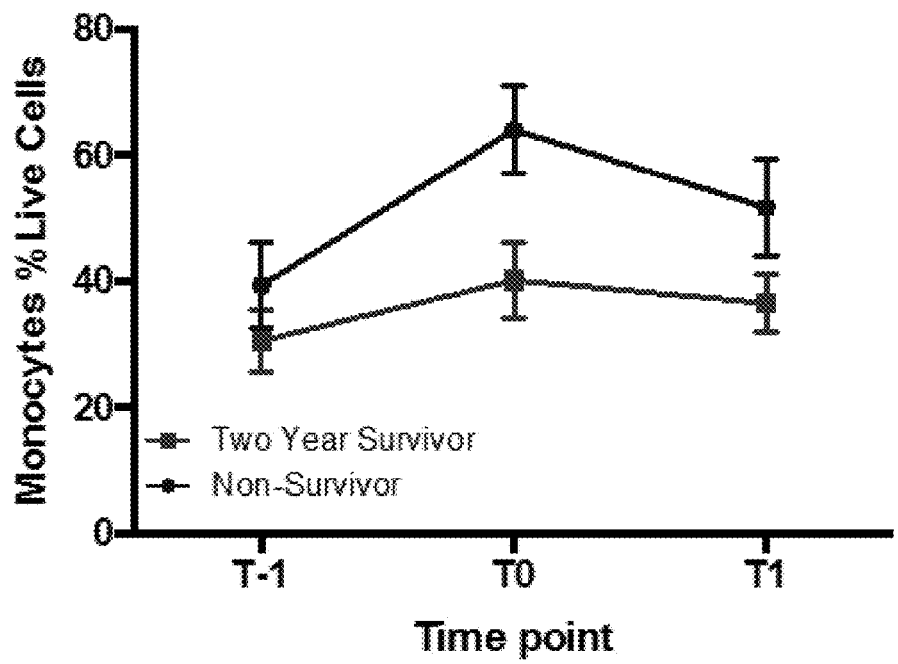

Discretization of patients based on two-year survival (non-survivors and two-year survivors) showed that monocyte numbers (as a proportion of leukocytes) were increased in both groups post-chemotherapy as compared to before chemotherapy (i.e. at T0 as compared to T-1), with the non-survivors showing the greater increase (FIG. 11A). These results were confirmed by flow cytometric analysis, however the rate of increase for two-year survivors was far less than observed by clinical whole blood counts (FIG. 11B). In both analyses, the number of monocytes in both groups was similar at two weeks post first immunotherapy (T1).

Figure 12A:
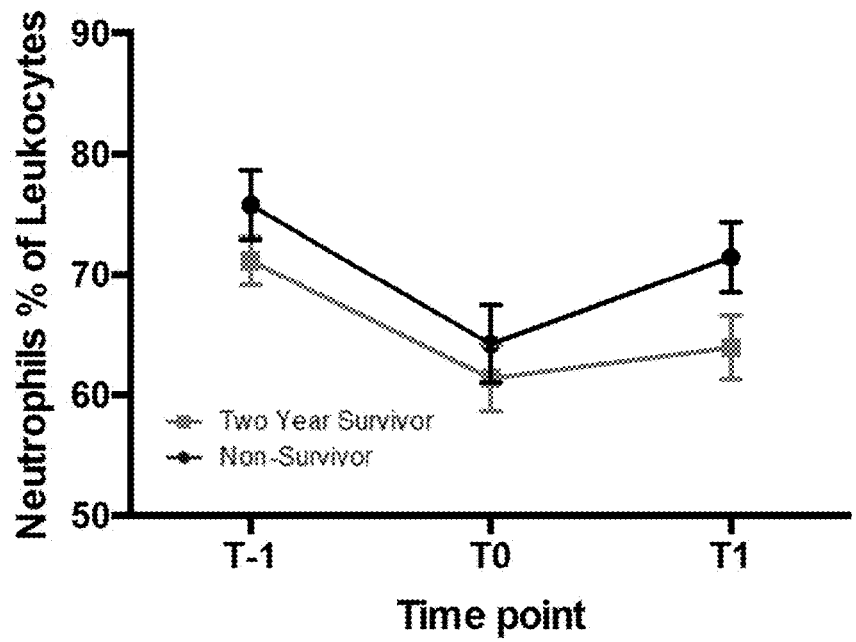
FIGS. 12A-12B. Graphs showing proportion of cell types as a percentage of leukocytes at different time points.
Figure 12B:
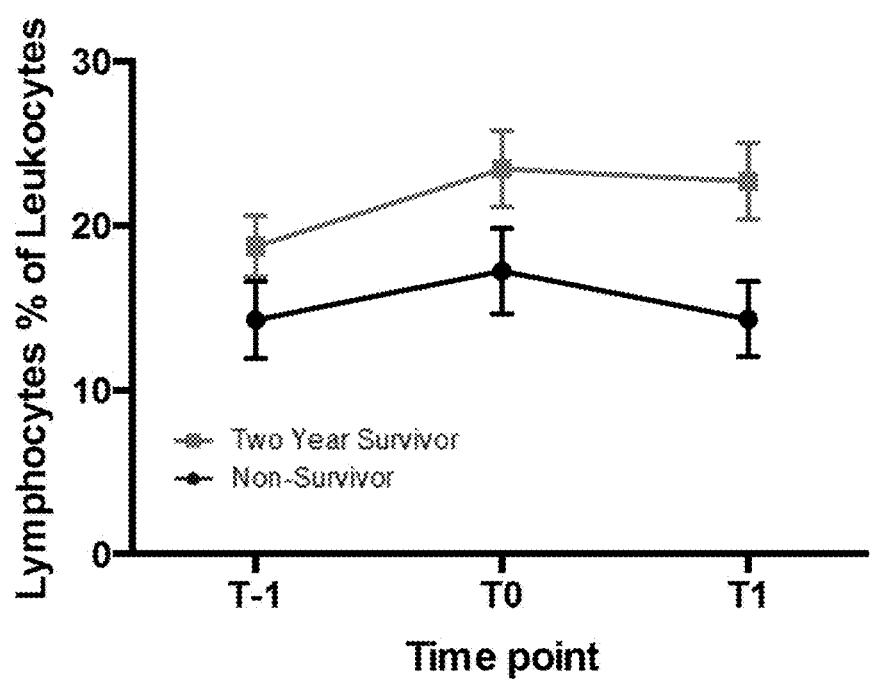

Conversely, time course analysis of the neutrophil compartment by two-year survival showed severe decreases in the number of neutrophils (as a proportion of leukocytes), which were not statistically different between the groups (FIG. 12A). Differences were also observed in the lymphocyte compartment, with two-year survivors having increased numbers of lymphocytes (as a proportion of leukocytes) throughout the time course as compared to non-survivors (FIG. 12B).

Figure 13:
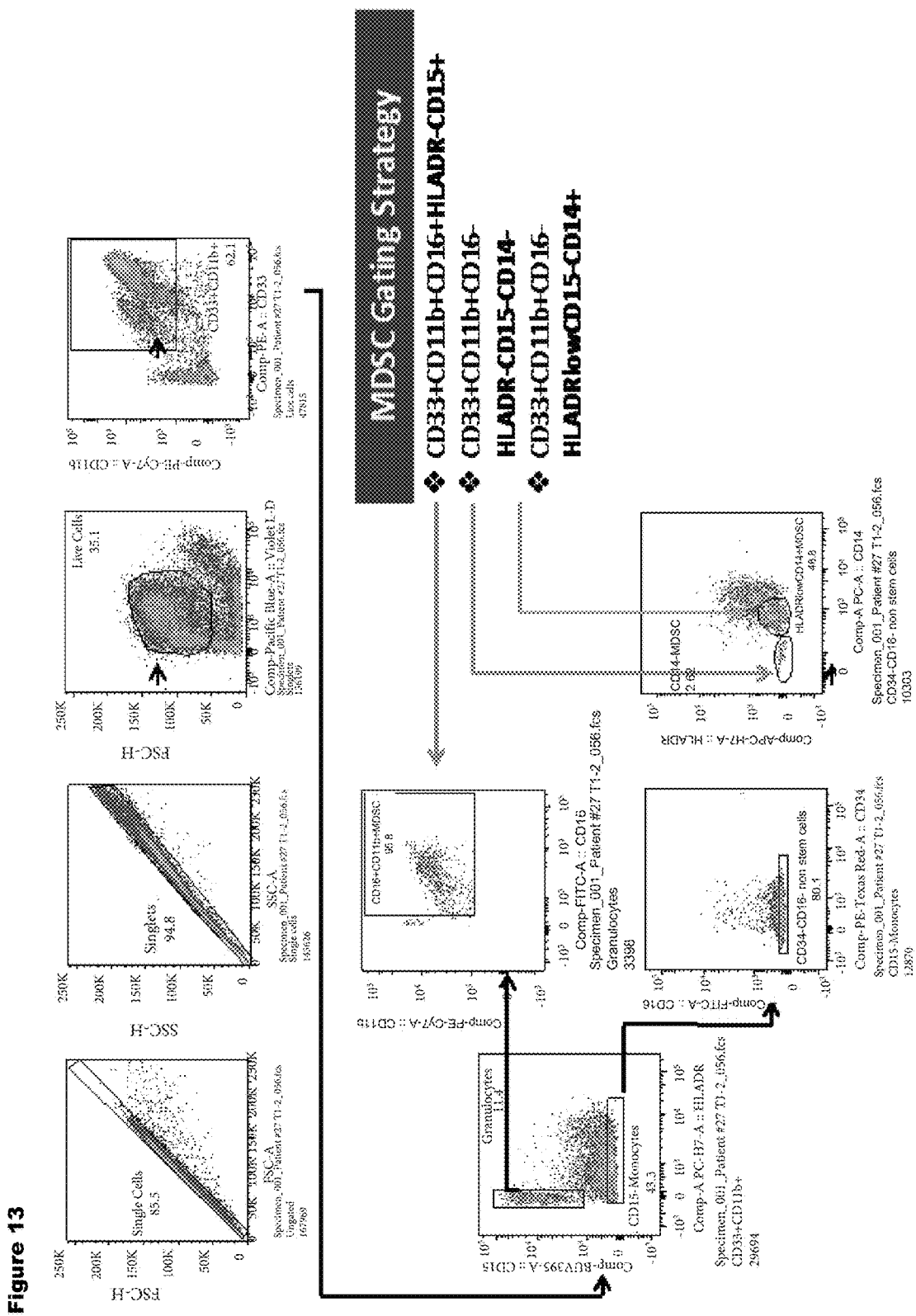
FIG. 13. Scatterplots showing gating strategy for MDSCs for flow cytometry.

The inventors next examined the phenotype of the peripheral, cryopreserved leukocytes, focusing in particular on monocytic-MDSCs and regulatory T-cells (FIG. 13). The time points examined were pre chemotherapy (T-1), post chemotherapy pre-immunotherapy (T0), post first CTL infusion (T1), post second CTL infusion (T2), and post third CTL infusion (T3).

Figure 14A:
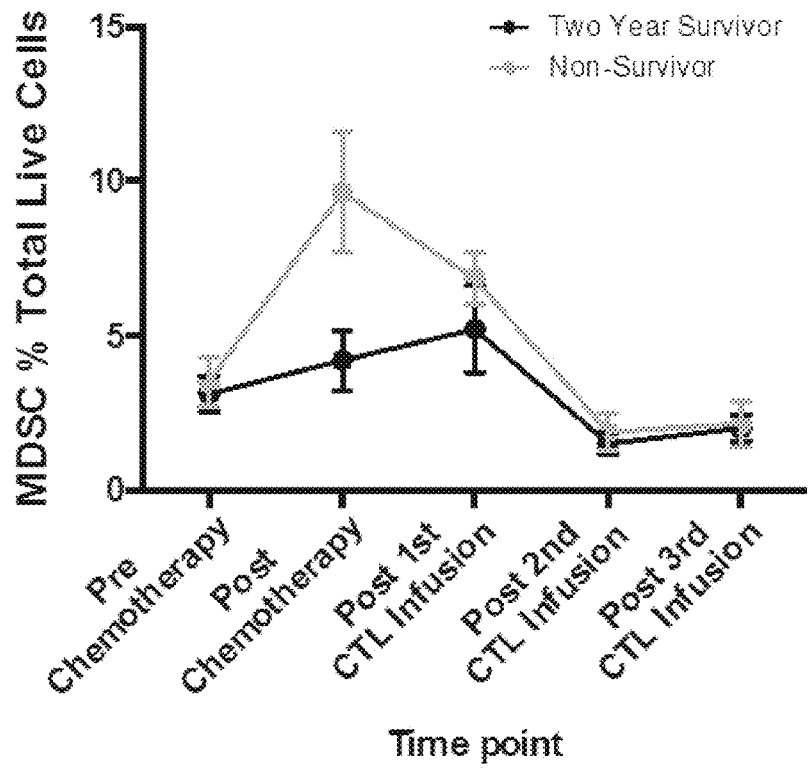
FIGS. 14A-14B. Graphs showing number of MDSCs as a percentage of the total number of live cells at different time points.
Figure 14B:
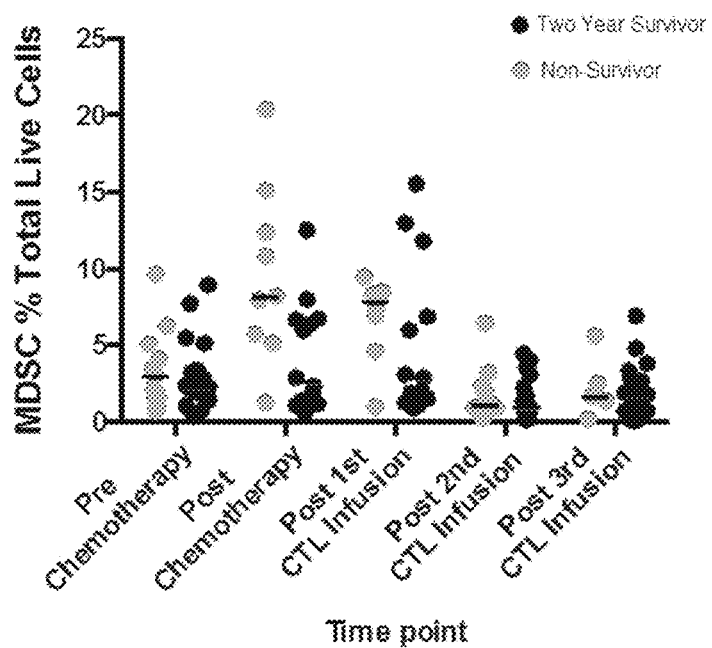

The proportion of MDSC at different time points as a proportion of the total number of live cells is shown in FIGS. 14A and 14B. No difference in MDSC numbers was observed between two-year survivors and non-survivors pre-chemotherapy (i.e. at T-1). After chemotherapeutic treatment at T0, a significant increase of MDSC numbers was observed in the non-survivors, whilst the long-term survivors exhibited a small but non-significant increase. Numbers of MDSCs in non-survivors then decreased but remained at levels above the number of MDSCs in long-term survivors (T1). At later time points the two groups of patients displayed comparable MDSC numbers, which were at levels below the pre-chemotherapy time point (FIGS. 14A and 14B). The results show that individuals who did not undergo successful immunotherapeutic treatment possess an increased number of monocytes, the majority of which were comprised of monocytic-MDSCs, at the time of first CTL infusion. The increased MDSC numbers at the time of first infusion may provide an inhibitory environment, thereby inhibiting the function of the infused CTLs.

Example 6: Long-Term Survivors with High MDSC Numbers Possess Decreased Numbers of Activated Tregs From the MDSC analysis it was noted that a subset of two-year survivors have high numbers of MDSCs post chemotherapy (>5.12% of live cells; see e.g. FIG. 14B), yet these individuals still underwent successful immunotherapeutic treatment. In order to investigate the role of other inhibitory leukocyte subsets that could account for this discrepancy, the cryopreserved PBMCs were also examined for regulatory T cell (Treg) numbers at different time points.

Figure 15:
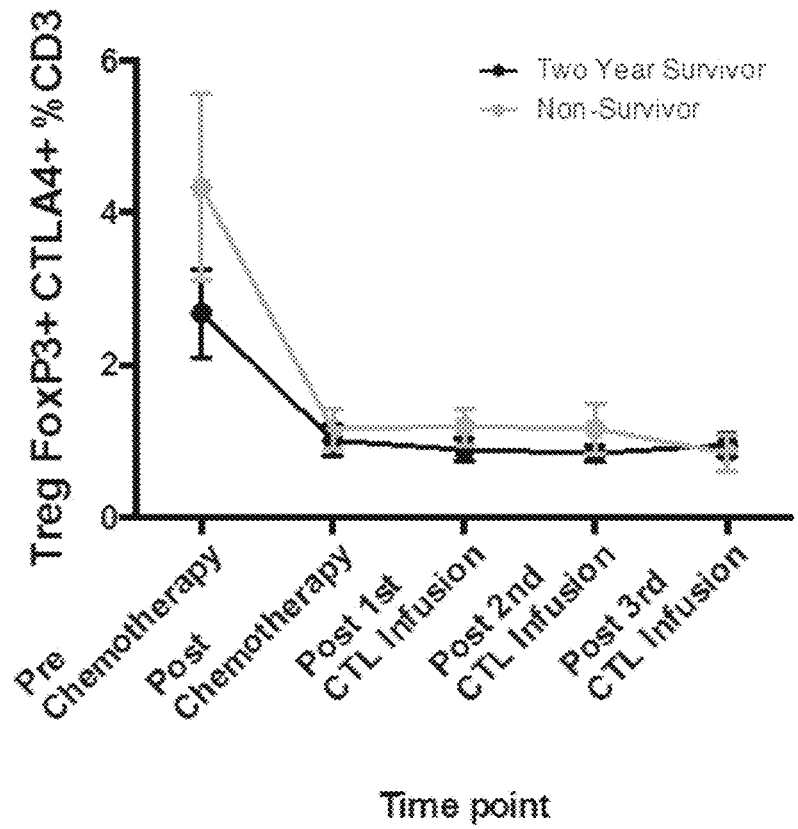
FIG. 15. Graph showing number of FoxP3+ CTLA4+ Tregs as a percentage of CD3+ cells at different time points.
Figure 16A:
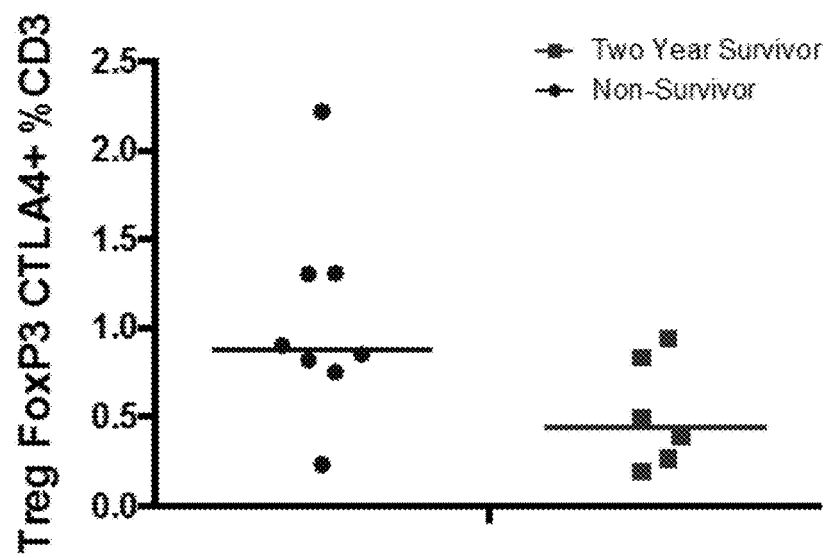
FIGS. 16A-16B. Graphs showing FIG. 16A FoxP3+ CTLA4+ Tregs as a percentage of CD3+ cells at T1 in patients with high numbers of MDSCs, and FIG. 16B FoxP3+ CTLA4+ Tregs as a percentage of CD3+ cells vs. overall survival.
Figure 16B:
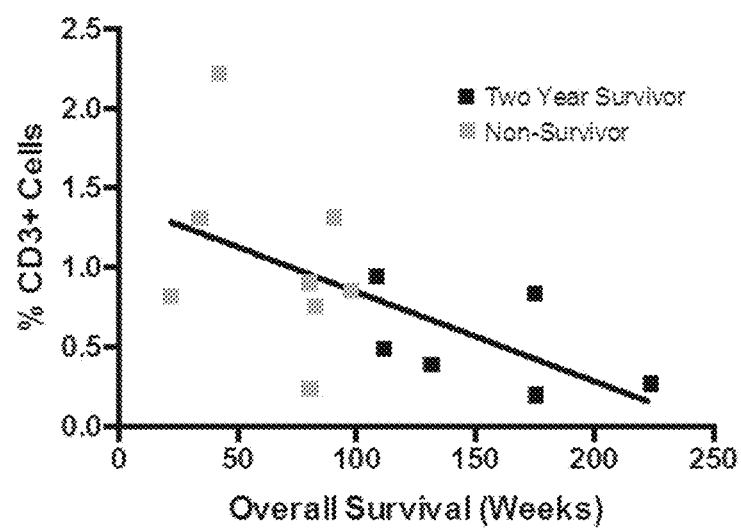

The results are shown in FIG. 15. The number of activated Tregs during the clinical trial was not significantly different between non-survivors and two-year survivors. Non-survivors did however display greater number of CTLA4+ Tregs before chemotherapy (i.e. at T-1). These numbers were decreased in both groups post chemotherapy (T0), with the non-survivors possessing slightly higher amounts of Tregs throughout the time course examined (FIG. 15). Examination of the subset of individuals with high numbers of MDSCs revealed a negative correlation between long-term survival and Treg numbers at time point T0, which might account for the successful therapy in the subset of two-year survivors having high numbers of MDSCs (FIGS. 16A and 16B).

Taken together these results show patients who survived for two years had decreased numbers of MDSCs and Tregs post chemotherapy, which allowed for the establishment potent CTL responses as evidenced by increased levels of IFNγ.

Example 7: Data Across all Time Points

The levels of IFNγ, CCL22, IL-10, IL-8, CCL20 (i.e. MIP3α) and VEGF determined in samples obtained from non-survivors and long-term survivors (i.e. more than 2 years) detected in samples obtained from patients at different time points over the course of the clinical trial were amalgamated and analysed.

Figure 17:
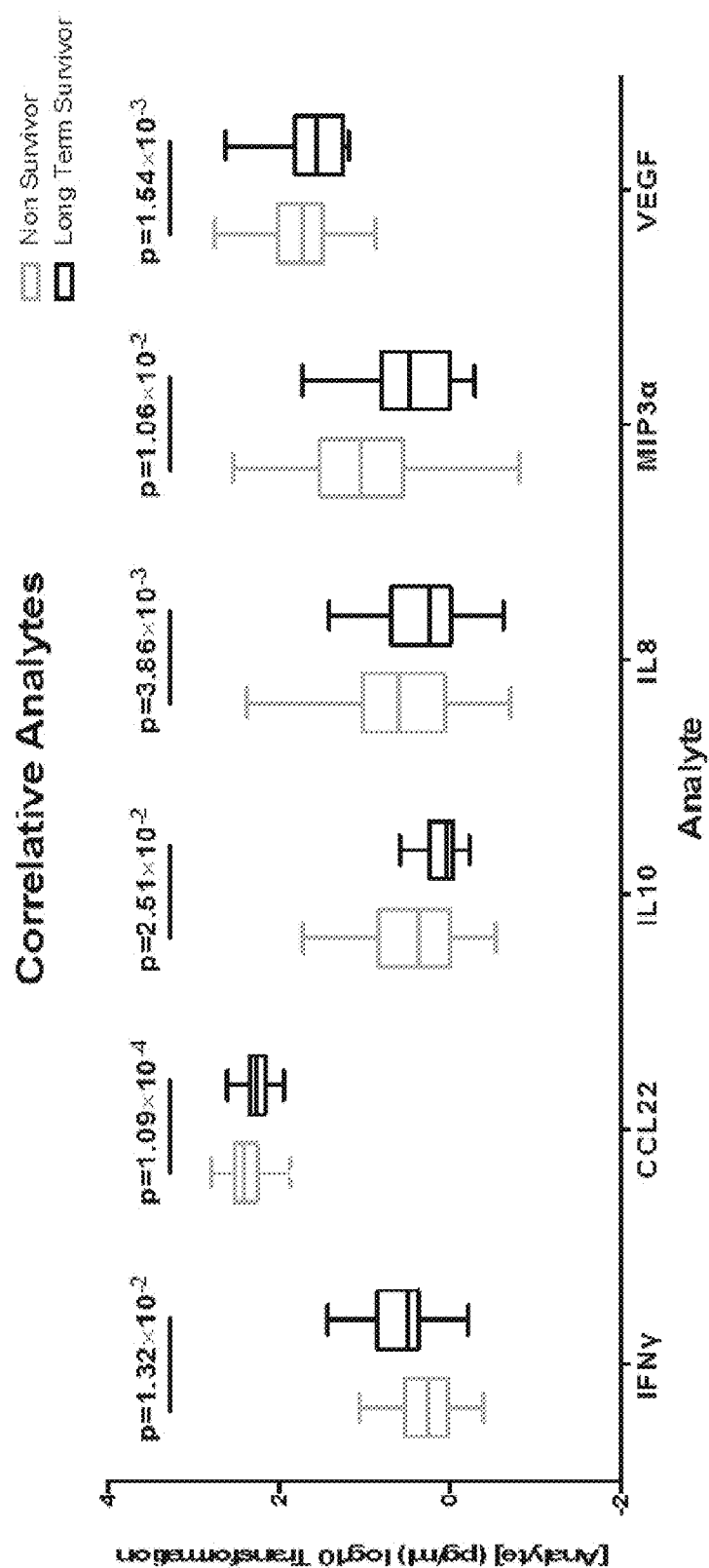
FIG. 17. Graph showing level of serum cytokines for non-survivors and long-term survivors (more than 2 years) across all time points.

The results are shown in FIG. 17, and show that the level of IFNγ positively correlated with long-term survival, whilst levels of each of CCL22, IL10, IL8, MIP3α and VEGF are negatively correlated with long-term survival.

REFERENCES

1. Chang, C. M., Yu, K. J., Mbulaiteye, S. M., Hildesheim, A. & Bhatia, K. The extent of genetic diversity of Epstein-Barr virus and its geographic and disease patterns: a need for reappraisal. Virus Res. 143, 209-221 (2009).
2. Wee, J. et al. Randomized trial of radiotherapy versus concurrent chemoradiotherapy followed by adjuvant chemotherapy in patients with American Joint Committee on Cancer/International Union against cancer stage III and IV nasopharyngeal cancer of the endemic variety. J. Clin. Oncol. 23, 6730-6738 (2005).
3. Gerdemann, U. et al. Nucleofection of DCs to generate Multivirus-specific T cells for prevention or treatment of viral infections in the immunocompromised host. Mol. Ther. 17, 1616-1625 (2009).
4. Chia, W. K. et al. A phase II study evaluating the safety and efficacy of an adenovirus-ΔLMP1-LMP2 transduced dendritic cell vaccine in patients with advanced metastatic nasopharyngeal carcinoma. Ann. Oncol. 23, 997-1005 (2012).
5. Moosmann, A. et al. Effective and long-term control of EBV PTLD after transfer of peptide-selected T cells. Blood 115, 2960-2970 (2010).
6. Louis, C. U. et al. Enhancing the in vivo expansion of adoptively transferred EBV-specific CTL with lymphodepleting CD45 monoclonal antibodies in NPC patients. Blood 113, 2442-2450 (2009).
7. Straathof, K. C. M. et al. Treatment of nasopharyngeal carcinoma with Epstein-Barr virus—specific T lymphocytes. Blood 105, 1898-1904 (2005).
8. Louis, C. U. et al. Adoptive transfer of EBV-specific T cells results in sustained clinical responses in patients with locoregional nasopharyngeal carcinoma. J. Immunother. 33, 983-990 (2010).
9. Smith, C. et al. Effective treatment of metastatic forms of Epstein-Barr virus-associated nasopharyngeal carcinoma with a novel adenovirus-based adoptive immunotherapy. Cancer Res. 72, 1116-1125 (2012).
10. Suzuki, E., Kapoor, V., Jassar, A. S., Kaiser, L. R. & Albelda, S. M. Gemcitabine selectively eliminates splenic Gr-1+/CD11b+ myeloid suppressor cells in tumor-bearing animals and enhances antitumor immune activity. Clin. Cancer Res. 11, 6713-6721 (2005).
11. Nowak, A. K., Robinson, B. W. S. & Lake, R. A. Gemcitabine exerts a selective effect on the humoral immune response: implications for combination chemo-immunotherapy. Cancer Res. 62, 2353-2358 (2002).
12. Shevchenko, I. et al. Low-dose gemcitabine depletes regulatory T cells and improves survival in the orthotopic Panc02 model of pancreatic cancer. Int. J. Cancer 133, 98-107 (2013).
13. Kan, S. et al. Suppressive effects of cyclophosphamide and gemcitabine on regulatory T-cell induction in vitro. Anticancer Res 32, 5363-5369 (2012).
14. Rettig, L. et al. Gemcitabine depletes regulatory T-cells in human and mice and enhances triggering of vaccine-specific cytotoxic T-cells. Int. J. Cancer 129, 832-838 (2011).
15. Wesolowski, R., Markowitz, J. & Carson, W. E., Ill Myeloid derived suppressor cells—a new therapeutic target in the treatment of cancer. 1, 1-1 (2013).
16. Dumitru, C. A., Moses, K., Trellakis, S., Lang, S. & Brandau, S. Neutrophils and granulocytic myeloid-derived suppressor cells: immunophenotyping, cell biology and clinical relevance in human oncology. Cancer Immunol. Immunother. 61, 1155-1167 (2012).
17. Filipazzi, P., Huber, V. & Rivoltini, L. Phenotype, function and clinical implications of myeloid-derived suppressor cells in cancer patients. Cancer Immunol. Immunother. 61, 255-263 (2011).
18. Ding, Z.-C. et al. Immunosuppressive myeloid cells induced by chemotherapy attenuate antitumor CD4+ T cell responses through the PD-1/PD-L1 axis. Cancer Res. (2014).doi:10.1158/0008-5472.CAN-13-3596
19. Huang, A. et al. Increased CD14+HLA-DR−/low myeloid-derived suppressor cells correlate with extrathoracic metastasis and poor response to chemotherapy in non-small cell lung cancer patients. Cancer Immunol. Immunother. 62, 1439-1451 (2013).

What is claimed is:

1. A method of treating an Epstein-Barr Virus (EBV)-positive cancer in a patient by adoptive cell transfer (ACT) of EBV-specific CTLs, the method comprising:
    (i) determining in a blood sample, or a plasma or serum sample derived from a blood sample obtained from the patient:
        (a) the ratio of the level of CXCL10 and/or CCL20 to the level of IFNγ, and
        (b) the ratio of the level of EBV nucleic acid to the level of IFNγ, and
    (ii) if said patient is determined to have (a) a ratio of the log 10-transformed level of CXCL10 in pg/ml to the log 10-transformed level of IFNγ in pg/ml of less than 2.5 and/or a ratio of the log 10-transformed level of CCL20 in pg/ml to the log 10-transformed level of IFNγ in pg/ml of less than 1.0, and (b) a ratio of the log 10-transformed level of EBV nucleic acid in pg/ml to the log 10-transformed level of IFNγ in pg/ml of less than 3.0, administering one or more doses of EBV-specific CTLs to the patient.

2. The method of claim 1, wherein the method additionally comprises an initial step of administering a dose of EBV-specific CTLs to the patient.

3. The method of claim 2, wherein the blood sample, or a plasma or serum sample derived from a blood sample is obtained from the patient within a period of 4 weeks after the initial step of administering a dose of EBV-specific CTLs to the patient.

4. The method of claim 1, wherein the EBV-positive cancer is selected from EBV-positive nasopharyngeal carcinoma (NPC), EBV-positive liver cancer, EBV-positive lung cancer, and EBV-positive gastric cancer.

5. The method of claim 1, wherein the EBV-positive cancer is EBV-positive NPC.

6. A method of treating an Epstein-Barr Virus (EBV)-positive cancer in a patient by adoptive cell transfer (ACT) of EBV-specific CTLs, comprising:
(i) determining in a blood sample, or a plasma or serum sample derived from a blood sample obtained from the patient:
    (a) the ratio of the level of CXCL10 and/or CCL20 to the level of IFNγ, and
    (b) the ratio of the level of EBV nucleic acid to the level of IFNγ;
(ii) based on step (i), predicting whether the patient will be a long-term survivor on treatment of the EBV-positive cancer by ACT of EBV-specific CTLs, wherein detection of (a) a ratio of the log 10-transformed level of CXCL10 in pg/ml to the log 10-transformed level of IFNγ in pg/ml of less than 2.5 and/or a ratio of the log 10-transformed level of CCL20 in pg/ml to the log 10-transformed level of IFNγ in pg/ml of less than 1.0, and (b) a ratio of the log 10-transformed level of EBV nucleic acid in pg/ml to the log 10-transformed level of IFNγ in pg/ml of less than 3.0 is predictive of long-term patient survival on treatment of the EBV-positive cancer by ACT of EBV-specific CTLs;
(iii) selecting a patient predicted to be a long-term survivor on treatment of the EBV-positive cancer by ACT of EBV-specific CTLs for treatment by ACT of EBV-specific CTLs; and
(iv) administering one or more doses of EBV-specific CTLs to the patient selected in step (iii).

7. The method of claim 6, wherein the method additionally comprises an initial step of administering a dose of EBV-specific CTLs to the patient.

8. The method of claim 7, wherein the blood sample, or a plasma or serum sample derived from a blood sample is obtained from the patient within a period of 4 weeks after the initial step of administering a dose of EBV-specific CTLs to the patient.

9. The method of claim 6, wherein the EBV-positive cancer is selected from EBV-positive nasopharyngeal carcinoma (NPC), EBV-positive liver cancer, EBV-positive lung cancer, and EBV-positive gastric cancer.

10. The method of claim 6, wherein the EBV-positive cancer is EBV-positive NPC.

11. A method of treating an Epstein-Barr Virus (EBV)-positive cancer in a patient by adoptive cell transfer (ACT) of EBV-specific CTLs, comprising:
(i) administering a dose of EBV-specific CTLs to the patient;
(ii) determining in a blood sample, or a plasma or serum sample derived from a blood sample obtained from the patient:
    (a) the ratio of the level of CXCL10 and/or CCL20 to the level of IFNγ, and
    (b) the ratio of the level of EBV nucleic acid to the level of IFNγ;
(iii) based on step (ii), predicting whether the patient will be a long-term survivor on treatment of the EBV-positive cancer by ACT of EBV-specific CTLs, wherein detection of (a) a ratio of the log 10-transformed level of CXCL10 in pg/ml to the log 10-transformed level of IFNγ in pg/ml of less than 2.5 and/or a ratio of the log 10-transformed level of CCL20 in pg/ml to the log 10-transformed level of IFNγ in pg/ml of less than 1.0, and (b) a ratio of the log 10-transformed level of EBV nucleic acid in pg/ml to the log 10-transformed level of IFNγ in pg/ml of less than 3.0 is predictive of long-term patient survival on treatment of the EBV-positive cancer by ACT of EBV-specific CTLs;
(iv) selecting a patient predicted to be a long-term survivor on treatment of the EBV-positive cancer by ACT of EBV-specific CTLs for treatment by ACT of EBV-specific CTLs; and
(v) administering one or more doses of EBV-specific CTLs to the patient selected in step (iv).

12. The method of claim 11, wherein the blood sample, or a plasma or serum sample derived from a blood sample is obtained from the patient within a period of 4 weeks after administering a dose of EBV-specific CTLs to the patient in step (i).

13. The method of claim 11, wherein the EBV-positive cancer is selected from EBV-positive nasopharyngeal carcinoma (NPC), EBV-positive liver cancer, EBV-positive lung cancer, and EBV-positive gastric cancer.

14. The method of claim 11, wherein the EBV-positive cancer is EBV-positive NPC.

* * * * *